US012761228B2

(12) United States Patent
Tijms et al.

(10) Patent No.: US 12,761,228 B2
(45) Date of Patent: Oct. 13, 2026

(54) METHODS AND MEANS FOR STRATIFICATION OF AN INDIVIDUAL SUFFERING FROM, OR SUSPECTED TO SUFFER FROM, A PROGRESSIVE NEURODEGENERATIVE DISEASE

(71) Applicant: Stichting VUmc, Amsterdam (NL)

(72) Inventors: Betty Marije Tijms, Alkmaar (NL); Pieter Jelle Visser, Amsterdam (NL); Kaj Ingemar Blennow, Kungsbacka (SE); John Henrik Zetterberg, Mölnlycke (SE); Per Johan Gobom, Gothenburg (SE)

(73) Assignee: Stichting VUmc, Amsterdam (NL)

( * ) Notice: Subject to any disclaimer, the term of this patent is extended or adjusted under 35 U.S.C. 154(b) by 699 days.

(21) Appl. No.: 17/599,316

(22) PCT Filed: Mar. 27, 2020

(86) PCT No.: PCT/NL2020/050216
§ 371 (c)(1),
(2) Date: Sep. 28, 2021

(87) PCT Pub. No.: WO2020/197399
PCT Pub. Date: Oct. 1, 2020

(65) Prior Publication Data

US 2022/0196683 A1 Jun. 23, 2022

(30) Foreign Application Priority Data

Mar. 28, 2019 (EP) .................................... 19165795

(51) Int. Cl.
*G01N 33/68* (2006.01)
*C07K 16/18* (2006.01)

(52) U.S. Cl.
CPC ......... *G01N 33/6896* (2013.01); *C07K 16/18* (2013.01); *G01N 2333/4709* (2013.01); *G01N 2800/2821* (2013.01)

(58) Field of Classification Search
CPC ....... G01N 33/6896; G01N 2333/4709; G01N 2800/2821; C07K 16/18
See application file for complete search history.

(56) References Cited

U.S. PATENT DOCUMENTS

2006/0094064 A1* 5/2006 Ray .................... G01N 33/6896 435/7.2
2012/0192298 A1* 7/2012 Weinstein .......... A01K 67/0276 435/325
2019/0091195 A1* 3/2019 Bacha .................... A61K 45/06

FOREIGN PATENT DOCUMENTS

WO 2011012672 A1 2/2011

OTHER PUBLICATIONS

Sui, Xiaojing, et al., "Cerebrospinal Fluid Biomarkers of Alzheimer's Disease," Neuroscience Bulletin, vol. 30, No. 2, pp. 233-242 (2014).

(Continued)

*Primary Examiner* — Rebecca M Fritchman
(74) *Attorney, Agent, or Firm* — Hoffmann & Baron LLP

(57) ABSTRACT

The invention relates to method for typing a sample of an individual suffering from, or is suspected to suffer from, a progressive neurodegenerative disease. The invention further relates to methods for assigning a treatment of the individual, based on said typing.

10 Claims, 4 Drawing Sheets

(56) References Cited

OTHER PUBLICATIONS

Figure 1:
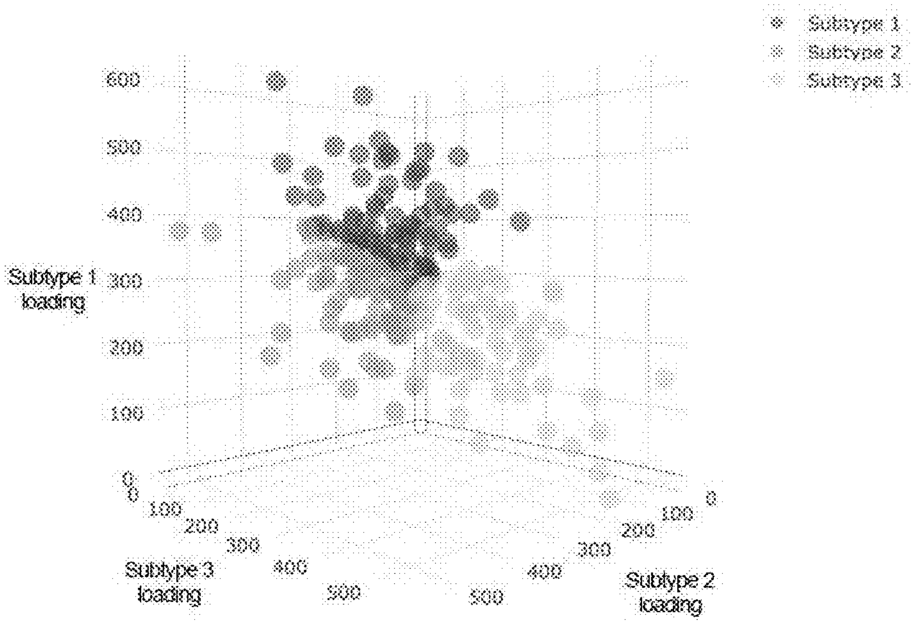
Figure 1:
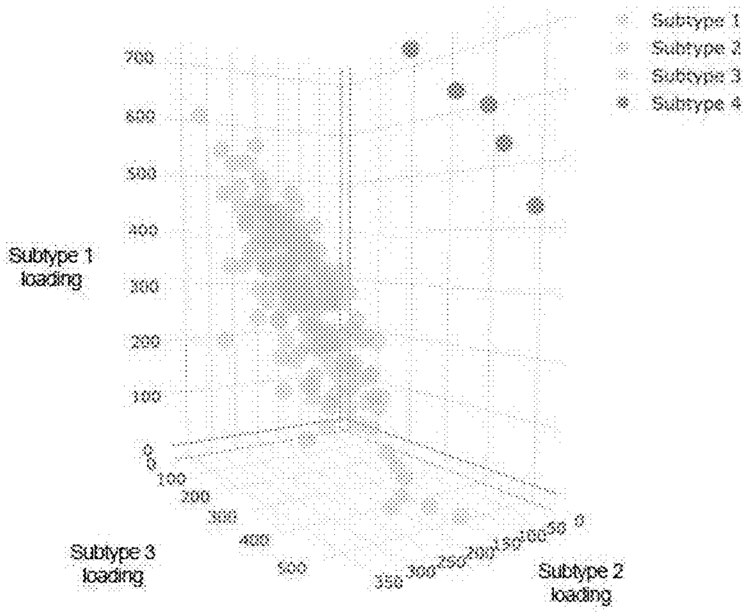

O'bryant, Sid E., et al. "Comparing Biological Markers of Alzheimer's Disease Across Blood Fraction and Platforms: Comparing Apples to Oranges," Alzheimer's & Dementia: Diagnosis, Assessment & Disease Monitoring, vol. 3, No. 1, pp. 27-34 (2016).
Del Campo, Marta, et al. "Novel CSF Biomarkers to Discriminate FTLD and Its Pathological Subtypes," Annals of Clinical and Translational Neurology, vol. 5, No. 10, pp. 1163-1175 (2018).
Teunissen, Charlotte E., et al. "Novel Diagnostic Cerebrospinal Fluid Biomarkers for Pathologic Subtypes of Frontotemporal Dementia Identified by Proteomics," Alzheimer's & Dementia: Diagnosis, Assessment & Disease Monitoring, vol. 2, pp. 86-94 (2016).

* cited by examiner

A

B

METHODS AND MEANS FOR STRATIFICATION OF AN INDIVIDUAL SUFFERING FROM, OR SUSPECTED TO SUFFER FROM, A PROGRESSIVE NEURODEGENERATIVE DISEASE

This application is the U.S. National Phase of, and Applicant claims priority from, International Patent Application Number PCT/NL2020/050216 filed 27 Mar. 2020, which claims priority from EP 19165795.6 filed 28 Mar. 2019, each of which is incorporated herein by reference.

FIELD OF THE INVENTION

The invention is in the field of biomarkers that may help to stratify individual suffering from, or suspected to suffer from, a progressive neurodegenerative disease.

1 INTRODUCTION

Alzheimer's disease (AD) is the most common cause of dementia. Abnormal levels of amyloid ß 1-42 (aß 1-42) and tau in cerebrospinal fluid (CSF) indicate the presence of AD's pathological hallmarks amyloid plaques and tau neurofibrillary tangles in the brain, and are part of the biological definition of AD (Jack et al., 2018. Alzheimer's Dementia 14: 535-562). This definition implies that AD is a single disease entity, however, individuals with AD show considerable variability in terms of clinical symptoms, age of onset, disease progression, cortical atrophy patterns, CSF tau levels and other pathological markers (Lam et al., 2013. Alzheimer's Research Therapy 5: 1; Möller et al., 2014. Neurobiol Aging 34: 2014-2022; Smits et al., 2015. Eur Neuropsychopharm 25: 1010-1017; Ossenkoppele et al., 2015. Hum. Brain Mapp 36: 4421-4437; Hondius et al., 2016. Alzheimer's Dementia 12: 654-668; van der Vlies et al., 2009. Neurology 72: 1056-1061; Wallin et al., 2010. Neurology 74: 1531-1537; Whitwell et al., 2012. Alzheimer's Dementia 8: P160-P161). Part of heterogeneity in AD is explained by genetic variance (Ridge et al., 2016. Neurobiol Aging 41: 200. e13-200. e20), suggesting that multiple biological pathways are involved in AD, including processes related to the innate immune system, lipid transport, synaptic functioning and endosomal-lysosomal pathways (European Alzheimer's Disease Initiative (EADI) et al., 2013. Nat Genet 45: 1452-1458). As such it is likely that patients may require personalised medicine, but at this point there are no tools to identify biological subtypes in AD in vivo. Cerebrospinal fluid (CSF) contains concentrations of thousands of proteins that reflect ongoing (patho)physiological processes in the brain, which may provide insight into biological processes contributing to heterogeneity in AD.

Targeted proteomics studies that studied heterogeneity in AD based on CSF amyloid, tau and p-tau levels suggest that at least three subtypes exist, which were mostly characterized by having low, intermediate or high tau levels (van der Vlies et al., 2009. Neurology 72: 1056-1061; Wallin et al., 2010. Neurology 74: 1531-1537). Additional biomarkers have been proposed in CSF or in blood to distinguish AD from controls (WO2011/012672; US2006/0094064; Xiaojing et al., 2014. Neuroscience Bulletin 30: 233-242) or within AD to distinguish between patients with higher versus lower mini-mental state examination (MMSE) scores (US2006/0094064).

Unbiased or large targeted analyses have the potential to further refine which biological processes may become disrupted in AD, but so far these studies have mostly focussed on discovering novel biomarkers by comparing AD individuals with controls and not on the identification of pathophysiological subtypes within AD patients (Maarouf et al., 2009. Curr Alzheimer Res 6: 399-406; Meyer et al., 2016. J Alzheimers Dis 63: 577-590). Thus it has not been studied yet whether biological subtypes exist within AD, and whether these can be identified with large scale gene expression analyses such as CSF proteomic analyses.

There is thus a need to identify biological AD subtypes. These subtypes may be suitable for stratification of AD patients in clinical trials and for a personalized medicine approach.

2 SUMMARY OF THE INVENTION

The invention provides a method for typing a sample of an individual suffering from a progressive neurodegenerative disease such as Alzheimer's disease (AD), comprising the steps of providing a sample from the individual, whereby the sample comprises gene expression products of said individual; determining a level of expression for at least three gene expression products listed in Table 2; comparing said determined levels of expression of each of the at least three gene expression products to a reference level of expression of each of the three gene expression products in a reference sample; and typing said sample on the basis of the comparison of the determined levels of expression level and the level of expression in a reference sample.

A dual clustering technique (non-negative matrix factorisation) was employed to identify biological subtypes of AD in CSF proteomics in two independent cohorts. Protein profiles were characterized in terms of biological processes involved through enrichment analyses, and AD subtypes were characterized in terms of clinical and biological characteristics known to be associated with AD, including CSF markers neurogranin, BACE1 activity, neurofilament light, YKL-40, sTREM2, APOE e4 genotype, cortical atrophy, and white matter hyperintensities. The specificity of these subtypes for AD was tested by repeating clustering in controls with normal cognition and normal CSF amyloid and tau biomarkers. Said sample from the individual preferably is or comprises a bodily fluid, preferably cerebrospinal fluid (CSF).

In preferred methods of the invention, a level of expression level for at least 6 gene expression products, at least 9 gene expression products, at least 12 gene expression products, preferably all 369 gene expression products listed in Table 2, is determined.

Said gene expression products preferably are proteinaceous molecules, most preferred are proteins. Preferred proteinaceous gene expression products are proteins indicated as CHGA, MASP1, and PLG in Table 2.

In an embodiment, a level of expression for at least three gene expression products is determined with the aid of an antibody or a functional part or equivalent thereof. Said antibody or a functional part or equivalent thereof is present on beads or on monolithic material.

In an embodiment, a level of expression for at least three gene expression products is determined by flow cytometric immunoassay (FOIA). Said level of expression for the at least three gene expression products preferably further comprises mass spectrometry.

The methods of typing according to the invention result in the classification of the individual into a hyperplastic, a neuroinflammation, or a blood brain barrier (BBB) dysfunction subgroup. Said typing further may result in the classification of the individual into a hyperplastic, a neuroinflammation, a blood brain barrier (BBB) dysfunction, or a fourth subgroup.

The invention further provides a method for assigning a ß-secretase (beta-site APP cleaving enzyme 1, BACE1) inhibitor to an individual, comprising the steps of typing a sample of the individual according to a method of the invention, and assigning a ß-secretase inhibitor to an individual that is classified in the hyperplastic subgroup.

The invention further provides a method for assigning an immune-modulating agent to an individual, comprising the steps of typing a sample of the individual according to a method of the invention, and assigning an immune-modulating to an individual that is classified in the neuroinflammation subgroup.

The invention further provides a method for assigning an anti-tau and/or anti-beta amyloid antibody to an individual, comprising the steps of typing a sample of the individual according to a method of the invention, and assigning an anti-tau and/or anti-beta amyloid antibody to an individual that is classified in the BBB dysfunction subgroup.

The invention further provides a method for assigning a block copolymer to an individual, comprising the steps of typing a sample of the individual according to a method of the invention, and assigning a block copolymer, preferably a block copolymer of poly(ethylene oxide) and poly(propylene oxide) and/or a gluccorticosteroid to an individual that is classified in the BBB dysfunction subgroup.

3 FIGURE LEGENDS

FIG. 1. Subject loadings on subtype scores for EMIF-AD MBD, without (A) and with 5 individuals with extreme loadings (B).

Figure 2:
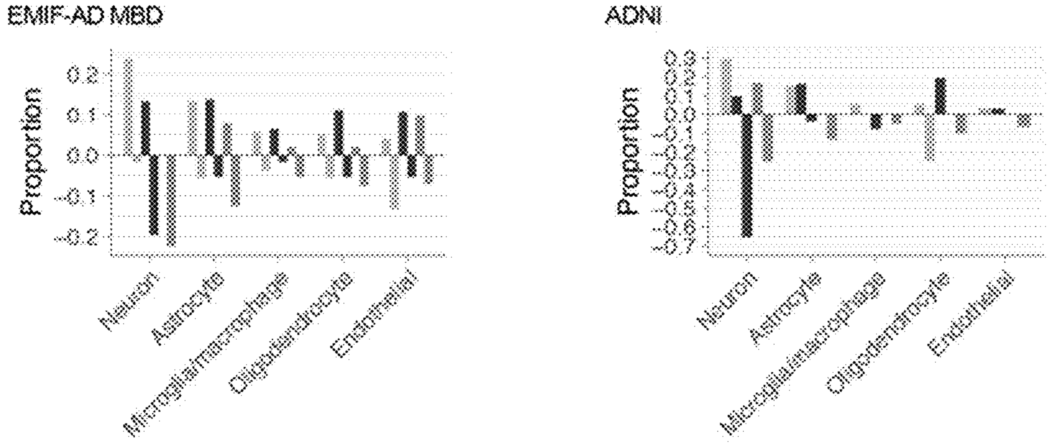

FIG. 2. Proportion of cell type production for protein levels higher (positive proportions) or lower than controls (negative proportions).

Figure 3:
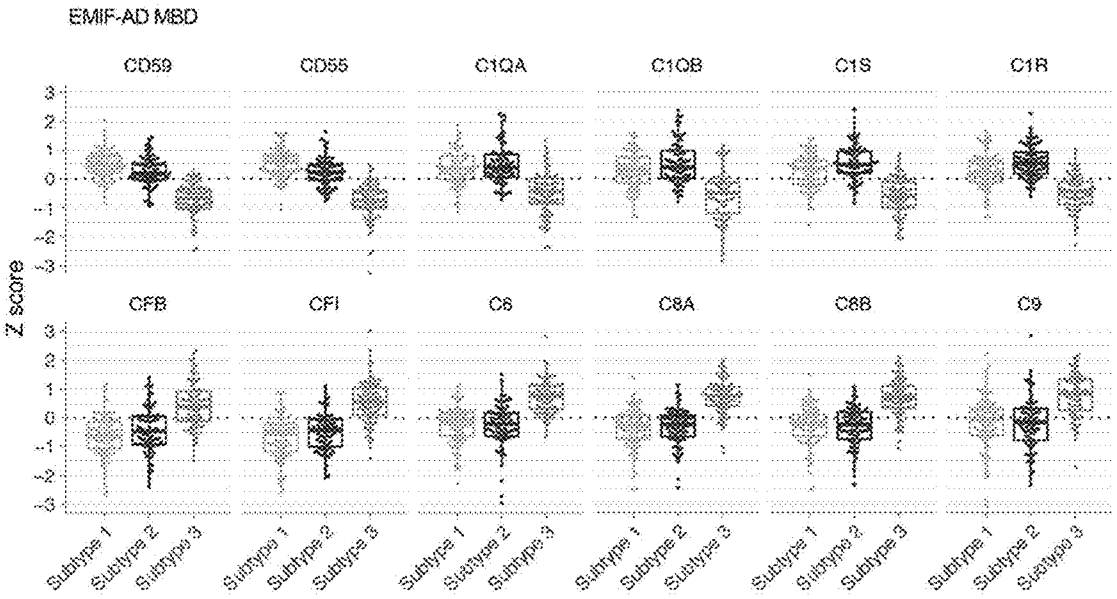

FIG. 3. Subtype differences in average levels of proteins associated with complement activation for EMIF-AD MBD. All protein levels were Z transformed according to the mean and standard deviation in controls, dotted line represents average protein levels for the control group.

Figure 4:
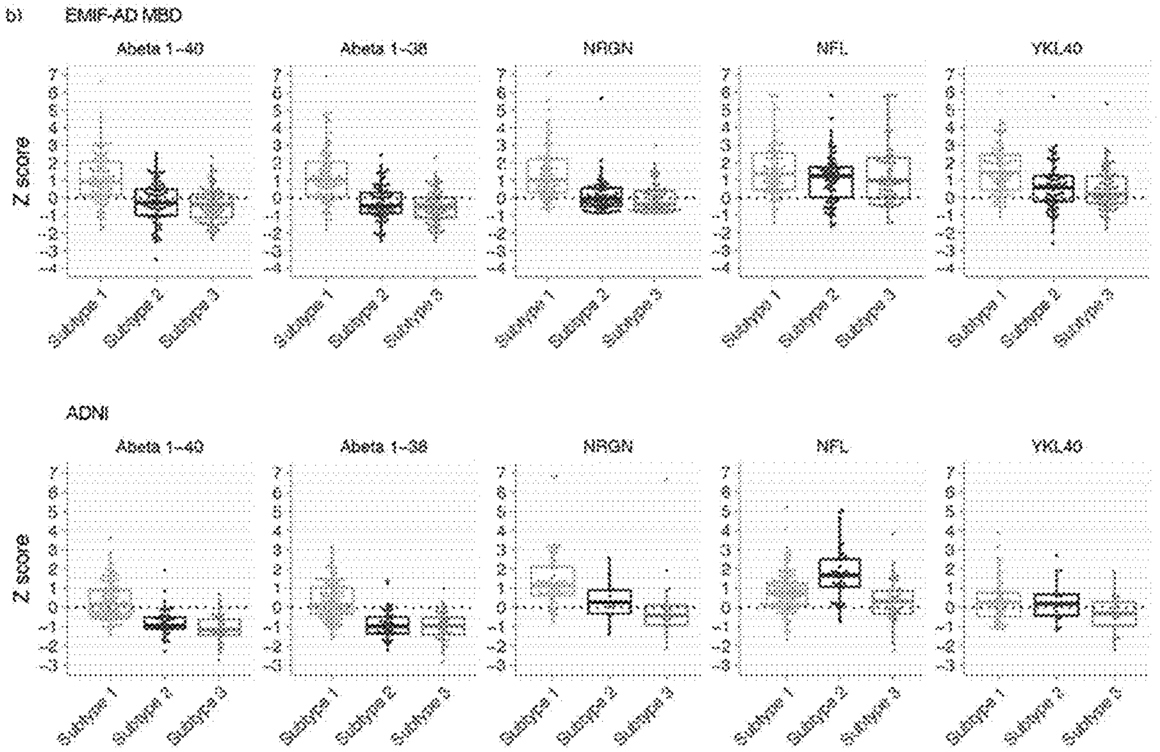

FIG. 4. CSF markers not included in clustering for EMIF-AD MBD (top row) and ADNI (bottom row).

4 DETAILED DESCRIPTION OF THE INVENTION

4.1 Definitions

The term "individual", as is used herein, refers to an individual who is suffering from, or is suspected to suffer from, a progressive neurodegenerative disease characterized by abnormalities in cognition, movement and behavior. Examples of such progressive neurodegenerative disease are Creutzfeldt-Jakob disease, Alzheimer's disease, vascular dementia and Lewy body dementia.

The term "Alzheimer's disease", as is used herein, refers to a neurodegenerative disorder of uncertain cause and pathogenesis that is the most common cause of dementia. Characteristics of Alzheimer's disease are deposits of beta-amyloid plaques and tau-containing neurofibrillary tangles in neocortical and subcortical regions of the brain. Beta-amyloid refers to peptides of 36-43 amino acids that are cleaved from an amyloid precursor protein (APP) by beta secretase and gamma secretase. Tau is a brain-specific, microtubule-associated protein. It is taught that misfolding of beta-amyloid and tau is a driving factor in Alzheimer's disease.

The term "sample", as is used herein, refers to a sample from an individual who is suffering from, or is suspected to suffer from, a neurodegenerative disease such as Alzheimer's disease. Said sample comprises gene expression products.

The term "gene expression product", as used herein, refers to an expression product of a gene and includes RNA, including mRNA, and protein.

The term "bodily fluid", as is used herein, refers to a liquid from or within a human body, including milk, blood, synovial fluid, urine, cerebrospinal fluid, bronchiolar lavage fluid, extracellular fluid including lymphatic fluid and transcellular fluid, tear fluid, and/or vitreous humor.

The term "cerebrospinal fluid", as is used herein, refers to a clear, colorless liquid that is present in the brain and spinal cord.

The term "reference sample", as is used herein, refers to a sample comprising gene expression products that is isolated from a healthy individual, and/or isolated from an individual that is known to suffer from Alzheimer's disease. More preferably, said reference sample is a pooled sample that comprises samples from multiple healthy individuals and/or from multiple healthy individuals that are known to suffer from Alzheimer's disease. It is preferred that said reference sample is pooled from more than 10 individuals, more preferred more than 20 individuals, more preferred more than 30 individuals, more preferred more than 40 individuals, most preferred more than 50 individuals.

The term "reference level", as is used herein, refers to a level of expression of one or more gene expression products in a reference sample. Said reference level preferably is displayed or outputted to a user interface device, a computer readable storage medium, or a local or remote computer system. The storage medium may include, but is not limited to, a floppy disk, an optical disk, a compact disk read-only memory (CD-ROM), a compact disk rewritable (CD-RW), a memory stick, and a magneto-optical disk.

The term "protein", as is used herein, refers to a class of gene expression products that can be used as biomarkers in methods of typing according to the invention. Suitable proteins for the methods of the invention are listed in Table 2. It will be clear to a person skilled in the art that a level of expression of a protein can be determined on the basis of a full length protein, or on the basis of one or more parts of a protein that are characteristic for that protein. The term protein, as is used herein, provides also reference to one or more parts of a protein that are characteristic for that protein.

The term "antibody", as used herein, refers to an immunoglobulin protein comprising at least a heavy chain variable region (VH), paired with a light chain variable region (VL), that is specific for a target epitope. A functional part of an antibody is defined herein as a part that has at least one shared property as said antibody in kind, not necessarily in amount. Non-limiting examples of a functional part of an antibody are a single domain antibody, a single chain antibody, a nanobody, an unibody, a single chain variable fragment (scFv), a Fd fragment, a Fab fragment and a F(ab')2 fragment. An equivalent of an antibody refers to an antibody mimetic such as a designed ankyrin repeat protein, a binding protein that is based on a Z domain of protein A, a binding protein that is based on a fibronectin type III domain, engineered lipocalin, and a binding protein that is based on a human Fyn SH3 domain (Skerra, 2007. Current Opinion Biotechnol 18: 295-304; ş krlec et al., 2015. Trends Biotechnol 33: 408-418).

The term "specifically recognizes and binds" refers to the interaction between an antibody, or functional part or functional equivalent thereof, and its epitope on a protein. This means that said antibody, or functional part or functional equivalent thereof, preferentially binds to said epitope over other antigens or amino acid sequences. Thus, although the antibody, functional part or equivalent may non-specifically bind to other antigens or amino acid sequences, the binding affinity of said antibody or functional part or functional equivalent for its epitope is significantly higher, preferably at least 5-fold higher, more preferred at least 10-fold higher than the non-specific binding affinity of said antibody or functional part or functional equivalent for other antigens or amino acid sequences. A higher binding affinity means that the equilibrium dissociation constant (KD) of an antibody or functional part or functional equivalent thereof for its epitope is significantly lower, preferably at least 5-fold lower, more preferred at least 10-fold ower than the KD for other antigens or amino acid sequences.

The term "PD1", as used herein, refers to a gene on human chromosome 2 that is also termed CD279, Programmed Cell Death 1, PDCD1 and Systemic Lupus Erythematosus Susceptibility 2. PD1 encodes a cell surface membrane protein. The term "PDL1", as used herein, refers to a gene on human chromosome 9 that is also termed CD274, Programmed Cell Death 1 ligand 1 and B7 homolog 1. PDL1 encodes a type I transmembrane protein.

The term "CTLA4", as used herein, refers to a gene on human chromosome 2 that is also termed Cytotoxic T-Lymphocyte-Associated Protein 4, CD2, CELIAC3, GSE, and CD152.

The term "glucocorticoid", as is used herein, refers to a steroid hormone that is produced in the zona fasciculata of the adrenal cortex. Glucocorticoids play a role in the immune system and are often used to treat individuals with an overactive immune system.

4.2 Samples and Detection Methods

A sample from an individual comprising gene expression products can be obtained in numerous ways, as is known to a person skilled in the art. In a method of the invention, a tissue sample is obtained directly from the individual, for example as a biopsy, for example from a part of the brain of the individual by craniotomy.

Said sample preferably is a bodily fluid, such as urine or blood. A preferred sample is or comprises cerebrospinal fluid, tear fluid, and/or vitreous humor, most preferred is or comprises cerebrospinal fluid.

A sample is collected from an individual and is treated to maintain the integrity, natural state of the gene expression products. Gene expression products can be prepared from freshly isolated cells or tissue at the moment of harvesting, or they can be prepared from stored cells or tissue, for example stored at −70° C., until processed for preparation of the gene expression products. Alternatively, a sample can be stored under conditions that preserve the quality of the protein or RNA gene expression products. Examples of these preservative conditions are the addition of inhibitors such as RNase inhibitors, for example RNAsin (Pharmingen) or RNasecure (Ambion), and/or proteinase inhibitors such as 4-(2-aminoethyl)benzene sulfonyl fluoride hydrochloride, bestatin, (1S,2S)-2-(((S)-1-((4-Guanidinobutyl) amino)-4-methyl-1-oxopentan-2-yl)carbamoyl)cyclopropane carboxylic acid, pepstatin A, phosphoramidon, leupeptin and/or aprotinin (Sigma-Aldrich).

A tissue sample preferably is disrupted for example by homogenization, for example by application of pressure, ultrasound or by mechanical homogenization, as is known to the skilled person, prior to preparation of the gene expression products.

Cells preferably are removed from a sample, for example by centrifugation. Centrifugation may be performed at low speed, such as between 2000×g and 5000×g, preferably at about 3000×g. Centrifugation preferably is performed at reduced temperature, preferably between 0° C. and 10° C., such as 4° C. Samples may also be pre-treated by ultracentrifugation.

A sample comprising blood such as a blood sample preferably is pre-treated by coagulation of platelets, for example at room temperature, followed by centrifugation at low speed, such as between 2000×g and 5000×g, preferably at about 3000×g. Centrifugation preferably is performed at a room temperature, preferably between 20° C. and 25° C.

A preferred sample comprises proteinaceous gene expression products, preferably proteins. A proteinaceous sample may be fractionated used standard techniques such as chromatography methods including ion exchange chromatography and/or size-exclusion chromatography, as is known to a person skilled in the art, prior to identification of the proteinaceous gene expression products as biomarkers in the methods of the invention.

Prior to identification, said proteinaceous gene expression products may be concentrated by affinity chromatography, for example by employing affinity partners such as antibodies or functional parts or equivalents thereof that bind specifically to one or more of the proteinaceous gene expression products listed in Table 2. Said concentration step in addition preferably removes any contaminants that may interfere with the subsequent detection of the proteinaceous gene expression products.

Several methods may be employed to concentrate said proteinaceous gene expression products by affinity chromatography or immunoprecipitation using, for example, affinity partners, such as antibodies or functional parts or equivalents thereof. It is preferred that the affinity partners such as antibodies or functional parts or equivalents thereof are coupled to a carrier material such as beads, preferably magnetic beads, or to monolithic material, preferably monolithic material that is embedded in columns, preferably in micro-columns.

The affinity partners may be coupled directly to the beads or monolithic material, or indirectly, for example by coupling of a second antibody that specifically recognizes one or more of the proteinaceous gene expression products. Said antibodies preferably are indirectly coupled to the beads or monolithic material by coupling of protein A, protein G, or a mixture of protein A and G to the beads or to the monolithic material. Said antibodies, preferably polyclonal antibodies, are preferably coupled to protein A-coupled beads or protein A-coupled monolithic material.

A proteinaceous sample comprising said proteinaceous gene expression products preferably is incubated with beads or monolithic material that are coupled to affinity partners under circumstances that allow binding of the proteinaceous gene expression products to the affinity partners on the beads or monolithic material. It is preferred that the proteinaceous sample is repeatedly incubated with the beads or monolithic material under circumstances that allow binding of the proteinaceous gene expression products to the affinity partners, preferably at least 2 times, more preferred at least 5 times, such as 10 times. Following the repetitive incubation steps, the beads or monolithic material are washed, for example with phosphate-buffered saline. Said washing step preferably also is repeated, preferably 2-20 times, more preferably about 10 times.

Following concentration of the proteinaceous gene expression products by affinity chromatography, the concentrated proteins are released from the affinity partners. Release may be accomplished by any method known in the art, including the application of a high pH buffer, a low pH buffer and/or a high salt buffer. Said elution step preferably is repeated. After collection of the eluate, a buffering solution preferably is added in order to neutralize the pH. The resulting eluate or eluates may be stored, for example at −20° C. or −80° C., until further use.

Whether or not said proteinaceous gene expression products have been concentrated, a level of expression of gene expression products, preferably of proteins as listed in Table 2, may be accomplished by any method known in the art. These methods include spectrometry methods such as high-performance liquid chromatography (HPLC) and liquid chromatography (LC), mass spectrometry (MS), including MS-MS (MS2) and MS3, and HPLC and LC that are coupled to MS (HPLC-MS, LC-MS, LC-(MS)2, and LC-(MS)3), and antibody-mediated methods such as flow cytometric immunoassay (FOIA).

Preferred methods allow parallel multiplexing of quantitative experiments. Such methods include mass spectrometry-based methods employing isobaric labeling strategies for relative quantitative proteomics such as Tandem Mass Tag (TMT), and Multiple Reaction Monitoring (MRM).

Isobaric chemical tags for relative and absolute quantitation (iTRAQ) and tandem mass tags (TMT) are commercially available, for example from Sigma-Aldrich (Saint Louis, MO) and AB Sciex Pte. Ltd. (Framingham, MA). Said isobaric labeling is coupled to mass spectrometry (MS), either as MS-MS (MS2) or as MS3 to provide an additional mass spectrum.

Multiple Reaction Monitoring (MRM) refers to the acquisition of data from specific product ions corresponding to multiple m/z selected precursor ions through two or more stages of mass spectrometry, thus involving (MS)2, (MS)3 or even additional mass spectrometry steps.

Further methods that also allow parallel multiplexing of quantitative experiments are antibody-based methods that simultaneously quantify multiple protein analytes in a single run, such as FCIA, including Luminex xMAP® technology.

FCIA involves the immobilization of a specific antigen from a sample on labeled microspheres with an unique dye through specific capture antigen-binding molecules. Binding of the antigen is detected with a detectable second antigen-binding molecule. The resultant mixture of microspheres, in which differently coloured microspheres are bound to different antigens, can be analyzed with a flow cytometer. Luminex xMAP®-based detection methods are commercially available, for example BioPlex® (BioRad, Hercules, CA) and Multi-Analyte Profiles (MAPs) (Myriad RBM, Austin, TX).

4.3 Gene Expression Products

The methods for typing a sample of an individual according to the invention comprise determining a level of expression for at least three gene expression products listed in Table 2. Said at least three gene expression products, preferably proteins, listed in Table 2 preferably comprise 1 protein from the group of proteins identified as 1-176 in the column termed “S1 ranking”, 1 protein from the group of proteins identified as 1-96 in the column termed “S2 ranking”, and 1 protein from the group of proteins identified as 1-97 in the column termed “S3 ranking”.

The methods for typing a sample of an individual according to the invention comprise determining a level of expression for at least six gene expression products listed in Table 2. Said at least six gene expression products, preferably proteins, listed in Table 2 preferably comprise 2 proteins from the group of proteins identified as 1-176 in the column termed “S1 ranking”, 2 proteins from the group of proteins identified as 1-96 in the column termed “S2 ranking”, and 2 proteins from the group of proteins identified as 1-97 in the column termed “S3 ranking”.

The methods for typing a sample of an individual according to the invention comprise determining a level of expression for at least nine gene expression products listed in Table 2. Said at least nine gene expression products, preferably proteins, listed in Table 2 preferably comprise 3 proteins from the group of proteins identified as 1-176 in the column termed “S1 ranking”, 3 proteins from the group of proteins identified as 1-96 in the column termed “S2 ranking”, and 3 proteins from the group of proteins identified as 1-97 in the column termed “S3 ranking”.

Preferred methods for typing a sample according to the invention comprise determining a level of expression for at least 18 gene expression products listed in Table 2. Said at least 18 gene expression products, preferably proteins, listed in Table 2 preferably comprise 6 proteins from the group of proteins identified as 1-176 in the column termed “S1 ranking”, 6 proteins from the group of proteins identified as 1-96 in the column termed “S2 ranking”, and 6 proteins from the group of proteins identified as 1-97 in the column termed “S3 ranking”.

Preferred methods for typing a sample of an individual according to the invention comprise determining a level of expression for at least 27 gene expression products listed in Table 2. Said at least 27 gene expression products, preferably proteins, listed in Table 2 preferably comprise 9 proteins from the group of proteins identified as 1-176 in the column termed “S1 ranking”, 9 proteins from the group of proteins identified as 1-96 in the column termed “S2 ranking”, and 9 proteins from the group of proteins identified as 1-97 in the column termed “S3 ranking”.

Preferred methods for typing a sample of an individual according to the invention comprise determining a level of expression for at least 45 gene expression products listed in Table 2. Said at least 45 gene expression products, preferably proteins, listed in Table 2 preferably comprise 15 proteins from the group of proteins identified as 1-176 in the column termed “S1 ranking”, 15 proteins from the group of proteins identified as 1-96 in the column termed “S2 ranking”, and 15 proteins from the group of proteins identified as 1-97 in the column termed “S3 ranking”.

Preferred methods for typing a sample of an individual according to the invention comprise determining a level of expression for at least 60 gene expression products listed in Table 2. Said at least 60 gene expression products, preferably proteins, listed in Table 2 preferably comprise 20 proteins from the group of proteins identified as 1-176 in the column termed “S1 ranking”, 20 proteins from the group of proteins identified as 1-96 in the column termed “S2 ranking”, and 20 proteins from the group of proteins identified as 1-97 in the column termed “S3 ranking”.

Said gene expression products, preferably proteins, listed in Table 2 preferably are selected according to the ranking indicated in Table 2.

Further preferred methods for typing a sample of an individual according to the invention comprise determining a level of expression for all 369 gene expression products listed in Table 2.

It is further preferred that genes used for typing a sample of an individual according to the invention are rank-ordered according to their contribution for correct typing of a particular subgroup.

Based on their ranking, preferred methods for typing a sample of an individual according to the invention comprise determining a level of expression for CHGA, MASP1, and PLG. As is shown in Table 3, the use of these gene expression products results in correct classification of Subtype 1 of 72.7%, correct classification of Subtype 2 of 67.7%, and correct classification of Subtype 3 of 79.2%, and an overall correct classification of 72.9%.

Further preferred methods for typing a sample of an individual according to the invention comprise determining a level of expression for CHGA, VSTM2A, MASP1, F5, PLG, and KNG1. As is shown in Table 3, the use of these gene expression products results in correct classification of Subtype 1 of 78.4%, correct classification of Subtype 2 of 70.3%, and correct classification of Subtype 3 of 80.8%, and an overall correct classification of 76.59%.

Further preferred methods for typing a sample of an individual according to the invention comprise determining a level of expression for CHGA, VSTM2A, CDH13, MASP1, F5, CTSD, PLG, KNG1, and SERPINF2. As is shown in Table 3, the use of these gene expression products results in correct classification of Subtype 1 of 80%, correct classification of Subtype 2 of 72.1%, and correct classification of Subtype 3 of 82.5%, and an overall correct classification of 78%.

Further preferred methods for typing a sample of an individual according to the invention comprise determining a level of expression for CHGA, VSTM2A, CDH13, VGF, MASP1, F5, CTSD, DCN, PLG, KNG1, SERPINF2, and AFM, or more preferred CHGA, VSTM2A, CDH13, VGF, CACNA2D1, MASP1, F5, CTSD, DCN, RNASE4, PLG, KNG1, SERPINF2, AFM, and ALB. As is shown in Table 3, the use of the latter gene expression products results in correct classification of Subtype 1 of 81.4%, correct classification of Subtype 2 of 76.2%, and correct classification of Subtype 3 of 82.9%, and an overall correct classification of 80%.

Based on their ranking, preferred methods for typing a sample of an individual according to the invention comprise determining a level of expression for CHGA, VSTM2A, CDH13, VGF, CACNA2D1, SLITRK1, MASP1, F5, CTSD, DCN, RNASE4, HTRA1, PLG, KNG1, SERPINF2, AFM, ALB, and C8A.

Further preferred methods for typing a sample of an individual according to the invention comprise determining a level of expression for CHGA, VSTM2A, CDH13, VGF, CACNA2D1, SLITRK1, ADGRB2, MASP1, F5, CTSD, DCN, RNASE4, HTRA1, LTBP2, PLG, KNG1, SERPINF2, AFM, ALB, C8A, and HABP2; more preferred CHGA, VSTM2A, CDH13, VGF, CACNA2D1, SLITRK1, ADGRB2, PTPRN2, MASP1, F5, CTSD, DCN, RNASE4, HTRA1, LTBP2, PROS1, PLG, KNG1, SERPINF2, AFM, ALB, C8A, HABP2, and GC.

Based on their ranking, preferred methods for typing a sample of an individual according to the invention comprise determining a level of expression for CHGA, VSTM2A, CDH13, VGF, CACNA2D1, SLITRK1, ADGRB2, PTPRN2, GFRA2, MASP1, F5, CTSD, DCN, RNASE4, HTRA1, LTBP2, PROS1, LTBP1, PLG, KNG1, SERPINF2, AFM, ALB, C8A, HABP2, GC, and SERPINC1.

Further preferred methods for typing a sample of an individual according to the invention comprise determining a level of expression for CHGA, VSTM2A, CDH13, VGF, CACNA2D1, SLITRK1, ADGRB2, PTPRN2, GFRA2, CBLN4, MASP1, F5, CTSD, DCN, RNASE4, HTRA1, LTBP2, PROS1, LTBP1, IGFBP7, PLG, KNG1, SERPINF2, AFM, ALB, C8A, HABP2, GC, SERPINC1, and C8B. As is shown in Table 3, the use of the latter gene expression products results in correct classification of Subtype 1 of 83%, correct classification of Subtype 2 of 79.2%, and correct classification of Subtype 3 of 86.4%, and an overall correct classification of 82.6%.

Further preferred methods for typing a sample of an individual according to the invention comprise determining a level of expression for CHGA, VSTM2A, CDH13, VGF, CACNA2D1, SLITRK1, ADGRB2, PTPRN2, GFRA2, CBLN4, HS6ST3, MASP1, F5, CTSD, DCN, RNASE4, HTRA1, LTBP2, PROS1, LTBP1, IGFBP7, OLFML3, PLG, KNG1, SERPINF2, AFM, ALB, C8A, HABP2, GC, SERPINC1, C8B, and APOA2.

Further preferred subsets of gene expression products, preferably proteins, comprise the top 12 ranked proteins for echt subset, the top 13 ranked proteins for echt subset, the top 14 ranked proteins for echt subset, the top 15 ranked proteins for echt subset. As is shown in Table 3, the use of the latter gene expression products results in correct classification of Subtype 1 of 83.5%, correct classification of Subtype 2 of 79.1%, and correct classification of Subtype 3 of 87.6%, and an overall correct classification of 83.3%.

Further preferred subsets of gene expression products, preferably proteins, comprise the top 20 ranked proteins for echt subset, or the top 30 ranked proteins for echt subset. As is shown in Table 3, the use of the latter gene expression products results in correct classification of Subtype 1 of 84.7%, correct classification of Subtype 2 of 83.1%, and correct classification of Subtype 3 of 88.1%, and an overall correct classification of 85.1%.

Based on their ranking, preferred methods for typing a sample of an individual according to the invention comprise determining a level of expression for CHGA, VSTM2A, CDH13, VGF, CACNA2D1, SLITRK1, ADGRB2, PTPRN2, GFRA2, CBLN4, HS6ST3, PTPRN, NRCAM, LY6H, TMEM132D, SCG2, NELL2, BASP1, PCSK1, CRTAC1, EPHA4, CGREF1, CHL1, GAP43, FAIM2, OPCML, CD99L2, FAM3C, VSTM2B, EPHA5, THY1, PRRT3, GDA, APLP1, CADM2, CACNA2D3, TNFRSF21, LYNX1, NPTX2, SEZ6L, PAM, CNTN3, TMEM132A, CNTNAP2, TGOLN2, MASP1, F5, CTSD, DCN, RNASE4, HTRA1, LTBP2, PROS1, LTBP1, IGFBP7, OLFML3, COL18A1, ECM2, C1S, CTBS, FMOD, FRZB, LAMB1, IGFBP2, MAN1C1, COLGA3, MSTN, C1R, OMD, PLTP, TTR, PCOLCE, SORT1, FBLN2, PTN, RNASET2, SPOCK1, LGALS1, SPOCK3, CTSB, NOV, COLGA1, PLXNB2, FBLNS, GALNT2, MMP11, MCAM, SELENOP, LRP1, FSTLS, PLG, KNG1, SERPINF2, AFM, ALB, CBA, HABP2, GC, SERPINC1, C8B, APOA2, APOA1, SERPINAG, SERPINA4, A1BG, CFB, F2, HPX, CPB2, SERPINA7, IGKV3D-11, IGKV3-11, APOH, APOM, PLGLA, C6, PON1, PLGLB1, SAA4, VTN, F12, CFI, MST1, IGKV3-20, IGHV3-7, MST1L, PODOX7, IGLC3, IGLC2, AZGP1, IGHG3, UACA, PODOXS, IGFALS, and IGHG1.

Further preferred subsets of gene expression products, preferably proteins, comprise the top 60 ranked proteins for echt subset, the top 75 ranked proteins for echt subset, and the top 90 ranked proteins for echt subset.

It is noted that the second column in Table 2, termed "related markers", denotes alternative gene expression products that may replace the gene expression product indicated in the first column as the contribution of the related gene expression product to the outcome is identical to the contribution of the gene expression product indicated in the first column to the outcome. For example, the second rank-ordered gene expression product Subtype 1, VSTM2A, can be replaced by VSTM2B, and the third rank-ordered gene expression product Subtype 1, CDH13, may be replaced by any one of CDH10; CDH11; CDH15; CDH2; and CDH8.

As is known to a person skilled in the art, the concentration of a gene expression product such as a protein may be normalized or standardized, for example according to a control group that includes age and sex matched individuals with intact cognition and normal amyloid beta 1-42 and tau biomarkers. Transformation of data according to a control group is to account for differences in the total amounts of gene expression products between two separate samples by comparing the level of expression of a gene or of multiple genes that is known not to differ in expression level between samples. Prior to statistical analyses protein levels may be normalized according to procedures as defined in the "Biomarkers Consortium CSF Proteomics MRM data set" in the "Data Primer" document available @adni.loni.ucla.edu, which are preferably used.

4.4 Methods of Typing According the Invention

The methods for typing a sample of an individual suffering from, or is suspected to suffer from, a progressive neurodegenerative disease characterized by abnormalities in cognition, movement and behavior according to the invention comprise the determination of a level of expression for at least three, preferably at least six, more preferably at least nine gene expression products listed in Table 2; and comparison of said determined levels of expression of each of the at least three, six or nine gene expression products to a reference level of expression of each of the three, six or nine gene expression products in a reference sample.

Typing of a sample can be performed in various ways. Said reference level of expression of each of the gene expression products in a reference sample may be a cut-off value. Cut-off values may then used, for example, in a decision tree approach such as Classification & Regression Trees (CART). It is shown herein below for the top 3 proteins how cut-offs for proteins can be determined and how these can be used to determine subtypes in AD patients.

As is indicated in Table 2, CHGA ranks highest (1) for S1 subtyping, with an average Z-transformed expression level in subtype 1 of +0.88, and of −0.05 and −0.9 in subtypes 2 and 3, respectively. CART analyses showed that individuals who have an average Z-transformed CHGA level higher than +0.05 may be typed as subtype 1.

MASP1 ranks 1 for S2 subtyping, with an average Z-transformed expression level in subtype 2 of +0.85, and +0.11 and −0.45 in subtypes 1 and 3, respectively. CART analyses showed that an individual with average Z-transformed CHGA level lower than +0.05, and an average Z-transformed MASP1 level lower than +0.34 may be typed as Subtype 3.

PLG ranks 1 for S3 subtyping, with an average Z-transformed expression level in subtype 3 of +0.74, and −0.65 and −0.5 in subtypes 1 and 2, respectively. CART analyses showed that an individual with average Z-transformed CHGA level lower than +0.05, an average Z-transformed MASP1 level higher or equal to +0.34 and an average Z-transformed PLG level lower than +0.5 may be typed as subtype 2.

CART analyses showed that an individual with an average Z-transformed CHGA level lower than +0.05, an average Z-transformed MASP1 level higher or equal to 0.34 and an average Z-transformed PLG level higher or equal to +0.5 is typed as subtype 3. CART analyses showed that an individual with average Z-transformed CHGA level lower than +0.05, an average Z-transformed MASP1 level lower than 0.34 and an average Z-transformed PLG level lower than 0.5 may be typed as subtype 1.

As an alternative, or in addition, said reference level of expression of each of the gene expression products in a reference sample is a profile template or multiple profile templates. A coefficient is determined that is a measure of a similarity or dissimilarity of a sample with a previously established reference gene expression level of the target genes in, for example, one or more individuals that were not known to suffer from a progressive neurodegenerative disease. Said established reference gene expression level of the target genes or reference profile includes the identity of the target genes, the method of determining expression levels of expression products of said target genes, the normalization method, if used, the determined expression levels of expression products of said target genes and the observed range of expression levels of expression products of said target genes in the group of individuals. Said reference profile preferably includes average Z-transformed expression levels of expression products of the target genes in the group of individuals.

Typing of a sample can be based on its (dis)similarity to a single profile template or based on multiple profile templates. In the invention, the profile templates are representative of samples that (i) are from one or more individuals that are not known to suffer from a progressive neurodegenerative disease characterized by abnormalities in cognition, movement and behavior, and/or (ii) are from one or more individuals that are known to suffer from a progressive neurodegenerative disease characterized by abnormalities in cognition, movement and behavior and have been typed as a Subtype 1, Subtype 2 or Subtype 3 individual. In some instances, said reference may also include a Subtype 4 profile template.

Preferably, the reference gene expression level is a template, preferably a profile template, indicative of an individual or group of individuals that is not known to suffer from a progressive neurodegenerative disease.

A number of different coefficients can be used for determining a correlation between the gene expression level in a sample from an individual and a profile template. Preferred methods are parametric methods which assume a normal distribution of the data. One of these methods is the Pearson product-moment correlation coefficient, which is obtained by dividing the covariance of the two variables by the product of their standard deviations. Preferred methods comprise cosine-angle, un-centered correlation and, more preferred, cosine correlation (Fan et al., Conf Proc IEEE Eng Med Biol Soc. 5:4810-3 (2005)).

Said correlation with a profile template is used to produce an overall similarity score for the set of genes that is used. A similarity score is a measure of the average correlation of gene expression levels of a set of genes in a sample from an individual and a profile template. Said similarity score can, but does not need to be, a numerical value between +1, indicative of a high correlation between the gene expression level of the set of genes in a sample of said individual and said profile template, and −1, which is indicative of an inverse correlation. A threshold can be used to differentiate between samples from an individual that is not likely to suffer from a progressive neurodegenerative disease, and samples from an individual that is likely to suffer from a progressive neurodegenerative disease. Said threshold is an arbitrary value that allows for discrimination between samples from an individual that is likely to suffer from a progressive neurodegenerative disease, and an individual that is not likely to suffer from a progressive neurodegenerative disease. If a similarity threshold value is employed, it is preferably set at a value at which an acceptable number of individuals that are likely to suffer from a progressive neurodegenerative disease would score as false negatives, and an acceptable number of individuals that are not likely to suffer from a progressive neurodegenerative disease would score as false positives. A similarity score is preferably displayed or outputted to a user interface device, a computer readable storage medium, or a local or remote computer system.

The methods of typing according the invention result in the classification of the individual into a Subtype 1 subgroup, indicated as hyperplastic or hyperactivated, a Subtype 2 subgroup, indicated as neuroinflammation, or a Subtype 3 subgroup, indicated as blood brain barrier (BBB) dysfunction subgroup.

The identified subtypes are associated with distinct biological processes, i.e., hyperplastic (S1), inflammation (S2), and blood-brain barrier dysfunction (S3). These biological subtypes of Alzheimer's disease (AD) showed pronounced differences in levels of APP processing, neuronal injury markers, and inflammation, which are processes that are often associated with AD. Furthermore, a fourth subtype of individuals was observed, showing mostly abnormally low concentrations of YWHAE, PRDX1, PRDX4, PREDX6, TMP1, TMP2, and YWHAZ, proteins that are associated with oxidative stress (see Table 5).

Previous proteomics approaches have suggested three AD subtypes that were characterized by having low, intermediate and high tau values (van der Vlies et al., 2009. Neurology 72: 1056-1061; Wallin et al., 2010. Neurology 74: 1531-1537). Each of the presently identified subtypes shows a similar distinction in tau levels, indicating that the three AD subtypes differ from subtypes based on tau-expression levels.

The majority of AD individuals were classified as subtype 1 with hyperplasticity. These showed high levels for the majority of proteins, which were enriched for amyloid fibril formation, and for regulation of MAPK/ERK cascade, glucose metabolism, synaptic structure and function, axonal development, glycosylation, and also oxidative stress, which are all processes that are involved in synaptic plasticity. These individuals also showed high levels of markers presumed to reflect neuronal injury, i.e., t-tau, p-tau, neurogranin, VSNL1, and SNAP25 (Brinkmalm et al., 2014. Molecular Neurodegeneration 9: 53; Fagan and Perrin, 2012. Biomarkers Med 6: 455-476). Yet, in contrast to the assumption that neuronal injury markers increase with disease severity, high levels of these proteins were already observed in very early AD stages when both cognition and cortical thickness were normal, and in even earlier stages when amyloid and tau were still normal. This calls into question whether high levels of these proteins reflect neuronal injury in these individuals, or, whether the high levels could also signify other (deregulated) processes. Previous studies have demonstrated that higher neuronal activity leads to increased tau (Pooler et al., 2013. EMBO Rep 14: 389-394; Yamada et al., 2014. J Exp Med 211: 387-393) and amyloid secretion (Cirrito et al., 2005. Neuron 48: 913-922; Bero et al., 2011. Nat Neurosci 14: 750-756), suggesting that coordinated increases of amyloid and tau may reflect synaptic activity. Disruptions in the balance of excitation and inhibitory synapses in neuronal circuits, potentially caused by amyloid oligomers, could lead to aberrant increased neuronal activation, possibly leading to a negative vicious cycle (Palop and Mucke, 2016. Nat Rev Neurosci 17: 777-792). This explanation seems supported by reports of hyperactive neurons in AD (Palop and Mucke, 2016. Nat Rev Neurosci 17: 777-792). Furthermore, this subtype seemed to be already present in the control group. These individuals showed higher levels of proteins associated with APP processing, and subsequent future aggregation of amyloid and p-tau levels. These results provide further support that amyloid overproduction may be the underlying cause for amyloid aggregation for a subset of individuals with AD. It is conceivable that this particular subtype most likely may benefit from treatments that inhibit APP processing, such as BACE inhibitors.

The inflammation subtype showed higher levels of proteins that were enriched for complement activation, extracellular matrix organization and oligodendrocyte development. In both cohorts, these individuals showed in particular high levels of complement proteins C1QB and C4A, and in EMIF-AD MBD also C1QA, C1QC, C1S, and C1R, which are part of the classical complement pathway. Amyloid beta fibrils are known to activate the complement pathway by binding to the C1Q complex (Rogers et al., 1992. Proc Natl Acad Sci USA 89: 10016-10020; Webster et al., 2002. J Neurochem 69: 388-398). Higher concentrations of C1Q and C4 in AD brains have been reported in pathological studies (Veerhuis et al., 2011. Mol Immunol 48: 1592-1603), and so higher concentrations of C4A might indicate complement activation in this subtype. Furthermore, complement activation might also play a role in neuronal injury in AD, because knocking out C1Q in APP mice attenuates both complement activation and neuronal injury (Zhou et al., 2008. J Neurochem 106: 2080-2092; Hong et al., 2016. Science 352: 712-716). This subtype showed higher levels clusterin (Fagan and Perrin, 2012. Biomarkers Med 6: 455-476), which is also associated with complement activation and is a genetic risk factor for AD (European Alzheimer's Disease Initiative, 2013. Nat Genet 45: 1452-1458). This subtype further showed enrichment for oligodendrocyte development, myelination processes (including CLU and CNTN2), and extracellular matrix organization (including MMP2), which are processes that are associated with activated microglia. Microglia secreting C1Q can induce so-called 'A1 reactive' astrocytes, which lose the ability to facilitate plasticity processes that promote cell survival, and accelerate death of neurons and oligodendrocytes (Liddelow et al., 2017. Nature 541: 481-487). Another factor that may lead to axonal damage is MMP2, which was increased in this subtype and is produced by microglia and oligodendrocytes (Diaz-Sanchez et al., 2006. Acta Neuropathol 111: 289-299). Furthermore, CNTN2 is produced by oligodendrocytes was specifically increased in this subtype. CNTN2 is a noncanonical notch ligand that may initiate remyelination processes. In multiple sclerosis (MS) CNTN2 has been observed to be expressed on demyelinating axons (Kremer et al., 2011. Annals Neurology 69: 602-618). In ADNI, this subtype showed an increased white matter hyperintensity volume, and in both EMIF-AD MBD and ADNI neurofilament light, an axonal cytoskeleton protein, was increased which may point towards axonal damage in this subtype. Possibly, this subtype would benefit from treatments that target microglia activation.

Subtype 3 showed low, mostly normal concentrations of tau and abnormal low levels of most other proteins. Current research criteria propose a biological definition of AD that requires both abnormal amyloid and abnormal tau markers (Jack et al., 2018. Alzheimer's Dementia 14: 535-562), raising the question as to whether these individuals have AD. These individuals had abnormal amyloid levels, and their patterns of atrophy and cognitive impairment were similar to the other two subtypes. A possibility is that these subjects harbour intraneuronal tau pathology, which can occur in the absence of abnormal total tau and p-tau levels in CSF (Tapiola et al., 2009. Arch Neurol 66: 382-389). The observation that most of increased levels of proteins in EMIF were of proteins not produced in the brain, such as albumin, points towards dysfunction of the blood-brain barrier. Possibly, blood-brain barrier dysfunction may lead to disturbed energy metabolism, leading to decreases in other proteins that are important for neuronal plasticity.

4.5 Methods of Treatment

As is known to a person skilled in the art, drugs as described herein below can be administered to an individual suffering from a progressive neurodegenerative disease such as Alzheimer's disease in an amount sufficient to at least partially halt the disease, and/or to reduce of halt any disease-associated complications. An amount adequate to accomplish this is defined as a "therapeutically effective dose." Amounts effective for this use will depend upon the severity of the disease and the general state of the individual's health. Single or multiple administrations of a ß-secretase inhibitor may be administered depending on the dosage and frequency as required and tolerated by the patient.

The invention further provides a method for assigning a ß-secretase (beta-site APP cleaving enzyme 1, BACE1) inhibitor to an individual suffering from a progressive neurodegenerative disease such as Alzheimer's disease, comprising the steps of typing a sample of the individual according to a method of typing according to the invention, and assigning a ß-secretase inhibitor to an individual that is classified in the hyperplastic Subgroup 1.

The invention further provides a ß-secretase (beta-site APP cleaving enzyme 1, BACE1) inhibitor for use in a method of treating an individual suffering from a progressive neurodegenerative disease such as Alzheimer's disease, said method comprising the steps of typing a sample of the individual according to a method of typing according to the invention, and assigning a ß-secretase inhibitor to an individual that is classified in the hyperplastic Subgroup 1.

The invention further provides an use of ß-secretase (beta-site APP cleaving enzyme 1, BACE1) inhibitor in the preparation of a medicament for treatment of an individual suffering from a progressive neurodegenerative disease such as Alzheimer's disease, whereby the individual is typed and classified in the hyperplastic Subgroup 1 according to a method of typing according to the invention.

Suitable ß-secretase inhibitors include verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide; Merck), at a dosage of 5-150 mg once or twice daily, preferably at 12-60 mg once or twice daily; lanabecestat ((1,4-trans,1'R)-4-methoxy-5"-methyl-6'-(5-(prop-1-yn-1-yl)pyridin-3-yl)-3'H-dispiro(cyclohexane-1,2'-indene-1',2"-imidazol)-4"-amine; AstraZeneca/Eli Lilly), at a dosage of 5-500 mg once or twice daily, preferably at about 50-150 mg once or twice daily; atabecestat (N-{3-[(4S)-2-Amino-4-methyl-4H-1,3-thiazin-4-yl]-4-fluorophenyl}-5-cyano-2-pyridinecarboxamide; Janssen), at a dosage of 2-250 mg once or twice daily, preferably at about 10-50 mg once or twice daily; and elenbecestat (N-{3-[(4a5,5R,7a5)-2-Amino-5-methyl-4a,5-dihydro-4H-furo[3,4-d][1,3]thiazin-7a(7H)-yl]-4-fluorophenyl}-5-(difluoromethyl)-2-pyrazinecarboxamide; Eisai/Biogen), at a dosage of 2-250 mg once or twice daily, preferably at about 5-50 mg once or twice daily.

Further drugs that may be assigned to an individual suffering from a progressive neurodegenerative disease such as Alzheimer's disease and who is typed and classified in the hyperplastic Subgroup 1 include antiepileptic drugs such as levetiracetam ((S)-2-(2-oxopyrrolidin-1-yl)butanamide), at a dosage of 30-200 mg once or twice per day, preferably at at a dosage of 50-150 mg once or twice per day; and valproate (2-propylpentanoic acid), at a dosage of 5-60 mg/kg once or twice per day, preferably at at a dosage of 10-50 mg once or twice per day.

Levetiracetam is available as an oral syrup, an intravenous infusion, and as immediate- and extended-release tablets. Valproate may be provided orally or intravenously.

The invention further provides a method for assigning an immune-modulating agent to an individual suffering from a progressive neurodegenerative disease such as Alzheimer's disease, comprising the steps of typing a sample of the individual according to a method of typing according to the invention, and assigning an immune-modulating to an individual that is classified in the neuroinflammation subgroup 2.

The invention further provides an immune-modulating agent for use in a method of treating an individual suffering from a progressive neurodegenerative disease such as Alzheimer's disease, said method comprising the steps of typing a sample of the individual according to a method of typing according to the invention, and assigning an immune-modulating agent to an individual that is classified in the neuroinflammation subgroup 2.

The invention further provides an use of an immune-modulating agent in the preparation of a medicament for treatment of an individual suffering from a progressive neurodegenerative disease such as Alzheimer's disease, whereby the individual is typed and classified in the neuroinflammation subgroup 2 according to a method of typing according to the invention.

Suitable immune-modulating agents include PD1, PDL1 and/or CTLA4 targeting antibodies, and a p38 MAPK inhibitor such as VX745 (neflamapimod; 5-(2,6-Dichlorophenyl)-2-[(2,4-difluorophenyl)sulfanyl]-6H-pyrimido[1,6-b]pyridazin-6-one, at a dosage of 20-200 mg once or twice per day, preferably at at a dosage of 40-125 mg once or twice per day.

Known antibodies that react with PD1 include nivolumab (BMS-936558; Bristol-Myers Squibb, Princeton, NJ), pembrolizumab (MK-3475; lambrolizumab; Merck & Co., Kenilworth, NJ), pidilizumab (CureTech Ltd., Yavne, Israel) and AMP224 and AMP514 (Amplimmune Inc., Gaithersburg, MD).

Known antibodies that react with PDL1 include BMS-936559 (previously MDX-1105; Bristol-Myers Squibb, Princeton, NJ), MSB0010718C (EMD-Serono; Merck KGaA, Darmstadt, Germany), MED14736 (AstraZeneca, London, UK), and MPDL 3280A (Roche, Basel, Switzerland).

Known antibodies that react with CTLA4 include ipilimumab (MDX-010 and MDX-101; Bristol-Myers Squibb, Princeton, NJ), tremelimumab (CP-675,206; Pfizer, New York, NY))

Antibodies against PD1, PDL1 and/or CTLA4 are preferably administered to an individual by parenteral injection and/or infusion, including intramuscular, intrapleural, intravenous, and subcutaneous injection and/or infusion. A typical treatment schedule or dosing regimen comprises parenteral administration, preferably intramuscular injection, of one dosage unit. The term "one dosage unit", as is used herein, refers to an effective amount of the antibody or antibodies, meaning an amount that produces an effect on the cancer to be treated.

A preferred dosage unit of antibodies to PD1, PDL1 and/or CTLA4 is between 0.1 and 20 mg/kg, preferably between 0.5 and 10 mg/kg. Said dosage unit preferably is applied daily, more preferred every second day, more preferred twice a week, more preferred once a week, more preferred every 2 weeks, more preferred every 3 weeks, more preferred once a month.

Antibodies to PD1, PDL1 and/or CTLA4 are preferably administered together with immune-stimulants. Said immune-stimulants may comprise recombinant, synthetic and natural preparations. Preferred immune-stimulants are interleukins (ILs) such as IL-2, IL-7, and/or IL-12, and interferons, but may also include imiquimod (3-(2-methylpropyl)-3,5,8-triazatricyclo[7.4.0.02,6]trideca-1(9),2(6),4,7,10,12-hexaen-7-amine), synthetic cytosine phosphate-guanosine (CpG), glucans, and/or the isolated membrane-bound product N-acetyl muramyl-L-alanyl-D-isoglutamine.

The invention further provides a method for assigning anti-tau antibodies and/or anti beta-amyloid antibodies to an individual suffering from a progressive neurodegenerative disease such as Alzheimer's disease, comprising the steps of typing a sample of the individual according to a method of typing according to the invention, and assigning said anti-tau antibodies and/or anti beta-amyloid antibodies to an individual that is classified in the blood-brain barrier (BBB) dysfunction subgroup 3.

The invention further provides anti-tau antibodies and/or anti beta-amyloid antibodies for use in a method of treating an individual suffering from a progressive neurodegenerative disease such as Alzheimer's disease, said method comprising the steps of typing a sample of the individual according to a method of typing according to the invention, and assigning anti-tau antibodies and/or anti beta-amyloid antibodies to an individual that is classified in the blood-brain barrier (BBB) dysfunction subgroup 3.

The invention further provides an use of anti-tau antibodies and/or anti beta-amyloid antibodies in the preparation of a medicament for treatment of an individual suffering from a progressive neurodegenerative disease such as Alzheimer's disease, whereby the individual is typed and classified in the the blood-brain barrier (BBB) dysfunction subgroup 3 according to a method of typing according to the invention.

Suitable anti-tau antibodies include gosuranemab (BIIB092; Biogen), ABBV-8E12 (AbbVie), RO7105705 (AC Immune SA/Genentech), LY3303560 (Eli Lilly & Co.), JNJ-63733657 (Janssen Pharmaceuticals, Inc), and UCB0107 (UCB S.A.).

Suitable anti beta-amyloid antibodies include bapineuzumab (Pfizer Inc./Janssen Pharmaceuticals Inc.), solanezumab (Eli Lilly & Co.), gantenerumab Chugai Pharmaceutical Co., Ltd./Hoffmann-La Roche), ponezumab (Pfizer Inc.), BAN2401 (Biogen/Eisai Co., Ltd.) and aducanumab (Biogen, Inc.).

Anti-tau and/or anti beta-amyloid antibodies are preferably administered to an individual by parenteral injection and/or infusion, including intramuscular, intrapleural, intravenous, and subcutaneous injection and/or infusion. A typical treatment schedule or dosing regimen comprises parenteral administration, preferably intravenous or intramuscular injection, of one dosage unit.

The term "one dosage unit", as is used herein, refers to an effective amount of the antibody or antibodies, meaning an amount that produces an effect on the cancer to be treated. A preferred dosage unit of anti-tau and/or anti beta-amyloid antibodies is between 0.1 and 60 mg/kg, preferably between 1 and 30 mg/kg. Said dosage unit preferably is applied daily, more preferred every second day, more preferred twice a week, more preferred once a week, more preferred every 2 weeks, more preferred every 3 weeks, more preferred every 4 weeks.

As will be clear to a person skilled in the art, said method for assigning anti-tau antibodies and/or anti beta-amyloid antibodies includes assigning active immunization therapy or vaccination therapy. In this therapy, the production of anti-tau and/or anti beta-amyloid antibodies in an individual is stimulated. For this approach, relevant fragments of tau and/or alpha amyloid may be provided to an individual in need thereof.

Examples of such active vaccination therapy include AADvac-1, comprising amino acid residues 294-305 of tau (Axon Neuroscience SE.), ACI-35, comprising amino acid residues 396-404 of tau (Immune SA/Janssen), CAD106, comprising alpha amyloid amino acid residues 1-6 (Novartis), ACC-001, comprising alpha amyloid amino acid residues 1-7 (Janssen), and Affitope, synthetic peptides mimicking the N-terminal part of alpha amyloid (Affiris AG.).

Said anti-tau and/or anti beta-amyloid vaccines are preferably administered to an individual by parenteral injection and/or infusion. A typical treatment schedule or dosing regimen comprises parenteral administration, preferably intravenous or intramuscular injection, of one dosage unit. A preferred dosage unit is between 10 and 250 microgram, preferably between 25 and 150 microgram.

The invention further provides a method for assigning a block copolymer and/or a glucorticoid to an individual suffering from a progressive neurodegenerative disease such as Alzheimer's disease, comprising the steps of typing a sample of the individual according to a method method of typing according to the invention, and assigning a block copolymer, preferably a block copolymer of poly(ethylene oxide) and poly(propylene oxide), and/or a glucocorticoid to an individual that is classified in the BBB dysfunction subgroup 3.

The invention further provides a block copolymer and/or a glucorticoid for use in a method of treating an individual suffering from a progressive neurodegenerative disease such as Alzheimer's disease, said method comprising the steps of typing a sample of the individual according to a method of typing according to the invention, and assigning a block copolymer and/or a glucorticoid to an individual that is classified in the blood-brain barrier (BBB) dysfunction subgroup 3.

The invention further provides an use of a block copolymer and/or a glucorticoid in the preparation of a medicament for treatment of an individual suffering from a progressive neurodegenerative disease such as Alzheimer's disease, whereby the individual is typed and classified in the the blood-brain barrier (BBB) dysfunction subgroup 3 according to a method of typing according to the invention.

Suitable block copolymers are known in the art, for example as described in Lee et al., 2018. Fluids Barriers CNS 15: 9 (doi: 10.1186/s12987-018-0094-5). A preferred block copolymer is a block copolymer of poly(ethylene oxide) and poly(propylene oxide).

Glucocorticoid are known to improve the tightness of the blood-brain barrier (Salvador et al., 2013. Cell Tissue Res 355: 597-605). Suitable glycocorticoids include one or more of cortisol ((8S,9S,10R,11S,13S,14S,17R)-11,17-dihydroxy-17-(2-hydroxyacetyl)-10,13-dimethyl-2,6,7,8,9,11,12,14,15,16-decahydro-1H-cyclopenta[a]phenanthren-3-one), cortisone ((8S,9S,10R,13S,14S,17R)-17-hydroxy-17-(2-hydroxyacetyl)-10,13-dimethyl-1,2,6,7,8,9,12,14,15,16-decahydrocyclopenta [a]phenanthrene-3,11-dione), prednisone ((8S,9S,10R,13S,14S,17R)-17-hydroxy-17-(2-hydroxyacetyl)-10,13-dimethyl-6,7,8,9,12,14,15,16-octahydrocyclopenta[a]phenanthrene-3,11-dione), prednisolone ((8S,9S,10R,11S,13S,14S,17R)-11,17-dihydroxy-17-(2-hydroxyacetyl)-10,13-dimethyl-7,8,9,11,12,14,15,16-octahydro-6H-cyclopenta [a]phenanthren-3-one), methylprednisolone ((6S,8S,9S,10R,11S,13S,14S,17R)-11,17-dihydroxy-17-(2-hydroxyacetyl)-6,10,13-trimethyl-7,8,9,11,12,14,15,16-octahydro-6H-cyclopenta[a]phenanthren-3-one), dexamethasone ((8S,9R,10S,11S,13S,14S,16R,17R)-9-fluoro-11,17-dihydroxy-17-(2-hydroxyacetyl)-10,13,16-trimethyl-6,7,8,11,12,14,15,16-octahydrocyclopenta[a] phenanthren-3-one), betamethasone ((8S,9R,10S,11S,13S,14S,16S,17R)-9-fluoro-11,17-dihydroxy-17-(2-hydroxyacetyl)-10,13,16-trimethyl-6,7,8,11,12,14,15,16-octahydrocyclopenta[a]phenanthren-3-one), triamcinolone ((8S,9R,10S,11S,13S,14S,16R,17S)-9-fluoro-11,16,17-trihydroxy-17-(2-hydroxyacetyl)-10,13-dimethyl-6,7,8,11,12,14,15,16-octahydrocyclopenta[a]phenanthren-3-one), fludrocortisone acetate ([2-[(8S,9R,10S,11S,13S,14S,17R)-9-fluoro-11,17-dihydroxy-10,13-dimethyl-3-oxo-1,2,6,7,8,11,12,14,15,16-decahydrocyclopenta[a]phenanthren-17-yl]-2-oxoethyl]acetate), and deoxycorticosterone acetate ([2-[(8S,9S,10R,13S,14S,17S)-10,13-dimethyl-3-oxo-1,2,6,7,8,9,11,12,14,15,16,17-dodecahydrocyclopenta[a] phenanthren-17-yl]-2-oxoethyl]acetate).

Said glucocorticoid preferably is for oral administrated of a dosage unit. A preferred dosage unit of a glucocorticoid is between 0.1 and 60 mg, preferably between 1 and 30 mg. Said dosage unit preferably is administered one or twice daily.

The invention further provides a method for assigning anti-tau antibodies and/or anti beta-amyloid antibodies to an individual suffering from a progressive neurodegenerative disease such as Alzheimer's disease, comprising the steps of typing a sample of the individual according to a method method of typing according to the invention, assigning said anti-tau antibodies and/or anti beta-amyloid antibodies to an individual that is classified in the BBB dysfunction subgroup 3, followed by assigning a block copolymer, preferably a block copolymer of poly(ethylene oxide) and poly(propylene oxide) to an individual that is classified in the BBB dysfunction subgroup 3.

As is known to a person skilled in the art, a large number of currently available drugs do not cross the blood-brain barrier. A remedy may be to administer the drug via a trans-cranial drug delivery system.

As an alternative, drugs can be transported using Trojan horse delivery systems to access receptor-mediated transport (RMT) systems within the BBB. For example, insulin variants and transferrin variants may be fused to a drug in order to transport the drug across the BBB. Said insulin variants preferably do not interfere with anabolic processes, and the transferrin variants do not interfere with free iron levels in biological fluids.

Further Trojan horse delivery systems may comprise antibodies or functional parts or equivalents thereof that bind epitopes on a BBB receptor. Fusion of said antibodies or functional parts or equivalents thereof may transport the drug across the BBB.

For the purpose of clarity and a concise description, features are described herein as part of the same or separate aspects and preferred embodiments thereof, however, it will be appreciated that the scope of the invention may include embodiments having combinations of all or some of the features described.

The invention will now be illustrated by the following examples, which are provided by way of illustration and not of limitation and it will be understood that many variations in the methods described and the amounts indicated can be made without departing from the spirit of the invention and the scope of the appended claims.

EXAMPLES

Example 1

Methods

Study Sample

For this study we selected 310 individuals from the European Medical Information Framework for Alzheimer's disease Multimodal Biomarker Discovery study (EMIF-AD MBD; Bos et al., 2018. Alzheimer's Res Therapy 10: 64), and 242 individuals from the Alzheimer's Disease Neuroimaging Initiative (ADNI, adni.loni.usc.edu) when they had CSF Aß42, tau, MRM and RBM proteomics and single protein data available (see CSF section for more details). ADNI started in 2003 as a public-private collaboration under the supervision of Principle Investigator Michael W. Weiner, MD. The primary goal of ADNI is to study whether serial magnetic resonance imaging (MRI), positron emission tomography (PET), other biological markers, and clinical and neuropsychological measures can be combined to measure the progression of mild cognitive impairment (MCI) and early Alzheimer's disease (AD). Please see @adni-info.org for the latest information. The institutional review boards of all participating institutions approved the procedures for this study. Written informed consent was obtained from all participants or surrogates.

Cerebrospinal Fluid Data

CSF samples were obtained as previously described (Toledo et al., 2013. Acta Neuropathol 126: 659-670; Bos et al., 2018. Alzheimer's Res Therapy 10: 64). CSF A642 and tau levels were measured with ELISAs (Alzbio or Innotest) for the EMIF-AD MBD data set, and with the multiplex xMAP® luminex platform (Luminex Corp, Austin, Texas) with the INNOBIA AlzBio3 kit (Innogenetics, Ghent, Belgium) for the ADNI dataset at the Biomarker Core laboratory at the University of Pennsylvania Medical Center. Cluster analyses were performed on proteomic data measured with Tandem Mass Tag (TMT) in EMIF-AD MBD, and in ADNI for 11 proteins determined with ELISAs, 311 protein fragments determined with Multi Reaction Monitoring (MRM) targeted mass spectroscopy, and 83 proteins measured with Rules Based Medicine (RBM) multiplex. Information on protein assessment and quality control is described @adni.loni.usc.edu/data-samples/biospecimen-data/. For MRM we used the finalized 'Normalized Intensity' data (Whitwell et al., 2012. Alzheimer's Dementia 8: P160-P161). Please see for detailed explanation of the normalization procedure the "Biomarkers Consortium CSF Proteomics MRM data set" in the "Data Primer" document @adni.loni.ucla.edu). A subset of individuals had 8 additional protein measurements with ELISAs available, and Aß40 and Aß38 measured with 2D-UPLC tandem mass spectrometry, and we used these as independent measurements to aid subtype interpretation. For controls we also studied longitudinal changes in Aß42 and tau, which were obtained from the same batch within each participant (n=610 CSF samples for 45 controls; median per person=3, min=2, max=6). In total, 708 proteins were considered for initial analyses in EMIF-AD MBD and 205 proteins in ADNI.

Cluster Analyses with Non-Negative Matrix Factorisation

First, we selected proteins for clustering that differed between the reference and AD groups at $p<0.10$ using Kruskal-Wallis tests (Kruskal and Wallis, 1952. J American Statistical Association 47: 583-621). Because protein levels can change non-linearly with levels of neuronal injury and/or disease severity (De Leon et al., 2018. PLoS ONE 13: e0191240; Duits et al., 2018. Alzheimer's Res Therapy 10: 387), we repeated analyses stratifying AD on cognitive stage, and on the presence of abnormal levels of the neuronal injury marker tau. Prior to cluster analyses all proteins were minimum-maximum normalised to have the same range of values between 0 and 1, since non-negative matrix factorisation requires non-negative data as input. Non-negative matrix factorisation is a dual clustering approach that is based on decomposition of the data by parts, as such reducing the dimensionality of data protein expression levels into fewer components which we consider protein profiles (Lee and Seung, 1999. Nature 401: 788-791). Protein profile scores indicate the contribution of proteins to the profile: high values suggest a stronger contribution, and values near 0 suggest no contribution of a protein to that profile. In order to aid the interpretation of the protein profiles we labelled proteins based on which subtype group showed the highest concentration. At the same time this algorithm groups subjects together into subtypes based on how well their protein expression levels match the protein profiles. We used the R package NMF for clustering, with the 'nonsmooth' option that ensures sparse cluster solutions with enhanced separability (Gaujoux and Seoighe, 2010. BMC Bioinformatics 11: 367). The optimal number of clusters was determined as the number of clusters for which: 1) The cophonetic correlation was high; 2) Fit compared to a lower cluster number solution was improved at least 2-fold over a random solution; and 3) Silhouette width of the cluster solution was >0.45. The NMF algorithm is stochastic and so subject classification to a subtype can vary from run to run, based on the random initial conditions. We assessed stability of subtype classification over 50 different runs of NMF with the co-phonetic coefficient with values ranging from 0 (i.e., unstable solution) to 1 (i.e., subjects are always classified the same). Clustering analyses were repeated in the control group to determine the specificity for AD of cluster solutions. We used the ANCOVA procedure to assess whether proteins significantly clustered differently for AD and controls subjects (Vidal et al., 2017. Front Neurosci 11: 321).

Subtype Classification Performance

First we selected the most important proteins for each subtype as determined with the 'max' method (Carmona-Saez et al., 2006. BMC Bioinformatics. 7: 78), which we used to test classification performance for decreasing protein set sizes (from 102 to 3 proteins). We trained random forest classifiers (Breiman, 2001. Machine Learning 45: 5-32) with these subsets of proteins on random selection of 70% of subjects, and tested classification performance on the left out 30% of subjects (repeated for 500 times), and calculated the overall and per subtype percentage correctly classified and the 95% confidence intervals.

Other Statistical Procedures

In order to test whether protein profiles were associated with specific biological processes, we performed pathway enrichment analyses for all proteins considered, and separately for each profile using the online Panther application (Mi et al., 2013. Nat Protoc 8: 1551-1566). Panther provides a nest/hierarchical representation of pathways enriched that are related in GO. We selected the pathways that were most consistently associated with the subtypes for visualisation. To determine cell type production we used the BRAIN RNASeq database (Zhang et al., 2014. J Neurosci 34: 11929-11947'see @brainrnaseq.org). We labelled proteins as being specifically produced by a certain cell type when the levels were higher than 50% of the total levels produced, as non-specific when none of the cell types was higher than 50%, or as not detected when protein levels were all <0.2. We compared individuals according to subtypes in terms of CSF levels of Aß42 and tau levels, 10 CSF proteins that were not included in the cluster analyses to provide further independent interpretation of the cluster solutions, age, gender, diagnosis, APOE e4 genotype, hippocampal volume, vascular damage (visual ratings in EMIF-AD MBD, and white matter hyperintensity volumes in ADNI), neuropsychological test scores in several cognitive domains (composites for EMIF-AD MBD; single tests for ADNI). memory (ADNI: memory immediate and delayed recall scores on the logical memory subscale II of the Wechsler Memory Scale), language (ADNI: Boston naming test), visuospatial processing (ADNI: Clock drawing) and attention/executive domains (digit span, Trail Making Test (TMT) a and TMT b), and cortical thickness measures from 34 cortical areas (averaged over the left and right hemispheres; as determined with Freesurfer in both EMIF-AD MBD and in ADNI (see @adni.loni.cule.edu for detailed documentation on variable specific methods). All continuous variables except for age were standardised according the mean and standard deviation of the control group. All subtype comparisons were performed with ANOVCAs and post-hoc adjustment for multiple testing with the Tukey procedure (Tukey, 1949. Biometrics 5: 99-114) in case of continuous variables, and with chi square tests for discrete variables. All comparisons for continuous variables were corrected for age and sex, and for cognitive measures additionally corrected for level of education. We used the R package 'emmeans' to obtain estimated marginalised means. ADNI data was downloaded on 30 Mar. 2018. All analyses were performed in R v3.5.1 'Feather spray'.

Results

Sample Description

We selected all individuals who had CSF proteomics data available from two multicentre studies, i.e., the EMIF-AD MBD (Bos et al., 2018. Alzheimer's Res Therapy 10: 64) and the ADNI, resulting in 131 controls with normal cognition and normal CSF AD markers, as based on centre-specific cut-points for EMIF-AD MBD, and in ADNI defined as having aß 1-42≥192 pg/ml, tau≤93 pg/ml (Shaw et al., 2009. Annals Neurology 65: 403-413) and 428 individuals with at least AD pathologic change defined as having abnormal CSF aß 1-42 levels (Jack et al., 2018. Alzheimer's Dementia 14: 535-562) across the cognitive spectrum, i.e., 89 (21%) with normal cognition, 198 (46%) with mild cognitive impairment (MCI) and 141 (33%) with dementia.

Compared to controls, individuals with AD more often carried an APOE e4 allele, and more often had abnormal p-tau and t-tau levels (data not shown). No differences were observed between these groups in sex, age or years of education in ADNI. Individuals with AD were older than controls in EMIF-AD MBD. For the proteomic data, individuals with AD showed differential CSF levels for 149 (73%) proteins in ADNI and for 556 (79%) proteins in EMIF-AD MBD compared to controls (data not shown). These proteins were considered for cluster analyses with non-negative matrix factorisation within in each cohort.

Three Biological Subtypes in AD Detected in CSF Proteomic Data

In both cohorts, three clusters best described the CSF proteomic data in terms of a highly stable assignment of individuals to subtypes as expressed by high cophonetic correlations ranging between 0.84 and 0.96, by average silhouette widths higher than 0.50, and up to 8 to 12% additional variance explained compared to a two-cluster solution (over two-fold additional variance explained compared to a random clustering solution). A 3D plot of subject loadings on clusters revealed in EMIF-AD MBD a subset of 5 individuals with extreme loadings (see FIG. 1 A, B). These individuals did not show clear differences with other AD subjects in the sample in terms of sample characteristics (Table 1). In order to avoid overfitting, we repeated cluster analyses excluding these individuals, and a three-cluster solution remained most optimal. We next labelled individuals according to the subtype they scored highest on. In both cohorts, the majority of individuals were labelled as having subtype 1 (80, 36% in EMIF; 117, 59% in ADNI), 71 (32%) were labelled as subtype 2 in EMIF and 41 (21%) in ADNI, 72 (32%) individuals were labelled as subtype 3 in EMIF and 39 (20%) in ADNI. Comparing subtypes on a subset of proteins (n=92) that were included in both ADNI and EMIF showed consistent subtype differences in levels for 84-98% of proteins, suggesting that the subtypes detected in both cohorts are robust (data not shown).

Individuals with subtype 1 had, when compared to controls, abnormally high levels for the majority of proteins in both cohorts (EMIF: 309, 56%; ADNI: 92, 65%). The majority of these proteins were produced by neurons and astrocytes (FIG. 2). GO pathway enrichment for proteins increased in subtype 1 showed involvement of processes associated with synaptic structure and function, axonal development, and glucose metabolism, pointing to synaptic dysfunction (data not shown).

TABLE 1

Descriptive comparison of controls with individuals with Alzheimer's disease from EMIF-AD MBD, stratified according to whether they were Included for the main analyses, or were Excluded as outlier

| | Controls | | Alzheimer's disease | |
|---|---|---|---|---|
| Descriptive | Included (n = 79) | Excluded (n = 3) | Included (n = 223) | Excluded (n = 5) |
| Cognitive status, n (%): | | | | |
| Normal cognition | 79 (100%) | 3 (100%) | 56 (25%) | 1 (20%) |
| Mild cognitive impairment | 0 (0%) | 0 (0%) | 90 (40%) | 2 (40%) |
| Dementia | 0 (0%) | 0 (0%) | 77 (35%) | 2 (40%) |
| Age in years, mean (sd) | 61.3 (7) | 57.3 (6.5) | 68.2 (8) | 66.0 (6) |
| Female, n (%) | 44 (56%) | 3 (100%) | 124 (56%) | 2 (40%) |
| Years of education, mean (sd) | 12.0 (3.5) | 10.0 (1.7) | 11.1 (3.5) | 13.6 (2.3) |
| MMSE, mean (sd) [1] | 28.6 (1.3) | 29.3 (1.2) | 25.5 (4.0) | 27.2 (2.2) |
| APOE e4, at least one allele (%) [2] | 13 (21%) | 1 (50%) | 138 (66%) | 5 (100%) |
| Hippocampal volume $cm^3$, mean (sd) | 8.0 (0.8) | n.a. | 6.7 (1.1) | 7.0 (0.7) |
| Aβ 1-42, mean (sd) [3] | 0.6 (0.7) | 0.8 (0.4) | −1.3 (0.6) | −1.7 (0.3) |
| T-tau, mean (sd) [3] | −0.4 (0.4) | 0 (0.3) | 1.2 (1.7) | 1.8 (1.1) |
| Abnormal t-tau, n (%) [4] | 0 (0%) | 0 (0%) | 146 (65%) | 5 (100%) |
| P-tau, mean (sd) [2, 3] | −0.24 (0.7) | −0.12 (0.2) | 1.1 (1.6) | 1.9 (1.4) |
| Abnormal p-tau, n (%) [4] | 7 (9%) | 0 (0%) | 144 (65%) | 5 (100%) |

MMSE is mini-mental state examination, APOE is Apolipoprotein E, n.a. is not available.

[1] is missing for 1 individual.

[2] is missing for 111 individuals.

[3] is scaled according to cohort specific controls as previously described (Bos et al., 2018. Alzheimer's Res Therapy 10: 64).

[4] cut points to define abnormal levels are cohort specific for EMIF-AD MBD as previously described (Bos et al., 2018. Alzheimer's Res Therapy 10: 64).

Groups were compared with Chi2 tests or t-test where appropriate, all p values were > .05.

Subtype 2 showed higher levels than controls for most proteins (EMIF: 202, 36%; ADNI: 31, 21%), which were mostly produced by oligodendrocytes, neurons and astrocytes. GO pathway enrichment for proteins increased in subtype 2 showed enrichment for complement activation, extracellular matrix organisation and oligodendrocyte development. In both ADNI and EMIF, clusterin was increased, in addition to the complement proteins C1Q and C4A. In EMIF additional increases in other complement proteins were observed, suggesting that this subtype is a neuroinflammation subtype.

Subtype 3 showed mostly decreased levels of proteins, when compared to controls, a pattern that mirrored the increases observed in subtype 1. The EMIF-AD MDB study showed the largest group of proteins that were increased in Subtype 3 compared to controls (ADNI 6, 4%; EMIF 51, 9%), and these included albumin, hemopexin and a group of immunoglobins. Many of those proteins are not produced in the brain, and showed enrichment for blood coagulation related processes such as fibrin cloth formation, hemostasis, and also B-cell activation and protein clearance. This suggests that this subtype may be characterised as having a blood brain barrier (BBB) dysfunction. This subtype also showed complement activation, but for a different group of proteins than observed in the inflammation subtype, including C6, C8A, C8B and C9 (see FIG. 3), which are not produced in the brain and provides further supports that this subtype may suffer from a BBB dysfunction as indicated for subtype 2.

We next compared subtypes on clinical, biological characteristics and on other CSF markers known to be associated with AD. Subtypes showed similar distributions of APOE e4 carriers in both cohorts (data not shown). In EMIF-AD MBD, subtypes also showed similar proportions of disease stages and sex and had comparable ages. In ADNI, individuals with subtype 1 less often had dementia, and individuals with subtype 2 were older and more often male. T-tau and p-tau CSF levels were highest and most often abnormal in the hyperplastic subtype 1, intermediate for the inflammation subtype 2, and lowest and most often normal in the BBB subtype 3 (see Table 6). Other neuronal injury markers neurogranin (both cohorts), VSNL1 and SNAP25 (ADNI only) were also highest in the hyperplastic subtype 1, and lowest in the BBB subtype 3. Levels of NFL were comparable between subtypes in EMIF, and highest for subtype 2 in ADNI.

The hyperplastic subtype 1 further showed higher levels of proteins associated with amyloid precursor protein (APP) processing, i.e., higher levels of BACE1 substrates Aß 1-40 and Aß 1-38 in both cohorts, and higher levels of BACE1 activity in ADNI (FIG. 4). The BBB dysfunction subtype 2 showed the lowest concentration of these markers. Both the hyperplastic and the inflammation subtypes showed higher levels of inflammation markers YKL-40 and sTREM2 (ADNI only) than the BBB dysfunction subtype (FIG. 4). Since some of these markers may increase with worsening disease severity, we repeated subtype comparisons stratified for disease stage (normal cognition (NC), mild cognitive impairment (MCI) and dementia), which resulted in largely similar subtype profiles, suggesting that subtype differences are not driven by disease severity (all pia >0.05; data not shown).

Atrophy, Vascular Damage and Cognitive Profiles

Cortical atrophy profiles as determined against controls showed for all subtypes most pronounced atrophy in the hippocampus, medial and lateral temporal cortex and the precuneus (data not shown). In ADNI more brain areas showed significant differences with controls and amongst subtypes than in EMIF-AD MBD. In both cohorts the most consistent subtype differences were observed in the dementia stage, with the BBB dysfunction subtype 3 and inflammation subtype 2 showing more atrophy in the posterior cingulate than the hyperplastic subtype (data not shown). The inflammation subtype 2 further showed more atrophy than the hyperplastic subtype in than inferior temporal gyrus, insula, isthmus cingulate, rostral middle frontal and temporal pole than hyperplastic subtype 1, which was also observed in mild cognitive impairment in ADNI (data not shown).

Stratified analyses according to tau abnormality status showed largely similar differences between subtypes. Visual ratings for vascular damage in EMIF showed that BBB-dysfunction subtype 3 more often had lacunar infarcts (n=10, 22%) than subtype 2 (1, 2%; p=0.006) and subtype 1 at trend level (4, 8%; p=0.08). No differences between subtypes were observed in having a Fazekas score (Fazekas et al., 1987. Am J Roentgenol 149: 351-6). of 3 (subtype 1: 2 (4%); subtype 2:6 (12%); subtype 3: 4 (9%), all p>0.05) or the presence of more than 1 microbleed (subtype 1: 5 (10%); subtype 2: 6 (15%); subtype 3: 6 (15%); all p>0.05). In ADNI, white matter hyperintensity volumes were higher in the BBB dysfunction subtype 3 (1.2±2.7 cm3) and the inflammation subtype 2 (1.3±1.4 cm3), as compared to the hyperplastic subtype 1 (0.85±3.0; p1vs2=0.0004; p1vs3=0.01; p2vs3=0.44). Subtypes showed no clear differences in the cognitive domains affected (data not shown), with the exception of the Trail Making Test (TMT)-a scores in ADNI, which were worst for the BBB subtype 3 in the dementia stage (psubtypeXdiagnosis=0.004).

CSF Proteomic Subtypes in the Control Group

We next performed cluster analyses of the proteins in controls to investigate whether the subtypes we detected were specific for AD. In controls three clusters best described the data for both ADNI and EMIF. This cluster solution in controls differed significantly from AD (both EMIF and ADNI: p<0.05). When comparing proteins profiles between the subtypes, subtype 1 showed, in comparison to subtype 3, higher levels for the majority of proteins (EMIF-AD MBD: 427, 77%; ADNI: 97, 53%), which mostly included proteins associated with synaptic structure and function. These proteins showed substantial overlap with those that differed between subtype 1 and 3 in AD (DICE coefficient of 0.74-0.99) (Table 4). Subtype 3 showed higher levels than the other subtypes for a large group of proteins (87, 16%) that were associated with blood brain barrier integrity in EMIF-AD MBD, similar as observed in AD. Subtype 2 differences against subtype 1 for EMIF-AD MBD (DICE 0.08) and against subtype 3 for ADNI (DICE=0.21) were inconsistent with subtype differences as compared to AD subtypes.

In EMIF-AD MBD and in ADNI no differences were found amongst subtypes in the proportion of APOE e4 carriers, and average age. EMIF-AD MBD subtype 1 showed a higher proportion of females than subtype 3 (p=0.02), whereas such differences did not reach significance in ADNI (p=0.28). When comparing subtypes on other CSF biomarkers, subtype 1 showed, in comparison to subtype 3, higher levels of BACE1 (ADNI only: p1vs3=0.03), and compared to subtype 2 and 3 higher levels of aß1-40 (p1vs2=0.0495; p1vs3=0.02) and aß1-38 (p1vs2=0.04; vs 3; p1vs3=0.004) in ADNI. This suggests that higher APP processing might be an early feature of AD in this subtype. Furthermore, subtype 1 showed higher p-tau levels than subtype 3 (significant only in EMIF: p1vs3=0.0499). In ADNI subtype 1 also showed higher levels of VSNL1 (p=0.009), and tended to show higher levels of SNAP 25 (p=0.08) and neurogranin (p=0.07) compared to subtype 3.

For ADNI repeated CSF aß 1-42, t-tau and p-tau measures were available (mean 3.2 (SD=1.2) samples over mean 3 (SD=1.9) years), which we used to further study associations of the subtypes with risk for developing AD, by comparing changes in CSF aß 1-42, t-tau and p-tau over time. Subtype 1 showed consistent decreases in aß 1-42 (6±SE=−4.4±1.9 pg/ml per year; p=0.03) and increases in p-tau (ß±SE=2.6±0.9 pg/ml per year; p=0.01). Subtype 2 showed increases in p-tau (ß±SE=−3.1±1.1 pg/ml per year; p=0.01) and t-tau (ß±SE=−2.2±1.0 pg/ml per year; p=0.03). Subtype 3 showed decreases in aß 1-42 (ß±SE=−5.6±2.0 pg/ml per year; p=0.009), and no changes in t-tau or p-tau. However, none of the slope estimates showed statistically significant differences between the subtypes (an p-interaction>0.10).

TABLE 2

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| CHGA | | P10645 | 0.8 | −0.05 | −0.9 | 1 | NA | NA |
| VSTM2A | VSTM2B | Q8TAG5 | 0.87 | 0.01 | −0.82 | 2 | NA | NA |
| CDH13 | CDH10; CDH11; CDH15; CDH2; CDH8 | P55290 | 0.91 | 0.09 | −0.79 | 3 | NA | NA |
| VGF | | O15240 | 0.54 | −0.3 | −1.2 | 4 | NA | NA |
| CACNA2D1 | CACNA2D2; CACNA2D3 | P54289 | 0.71 | −0.01 | −0.91 | 5 | NA | NA |
| SLITRK1 | SLIT1 | Q96PX8 | 0.76 | −0.07 | −0.9 | 6 | NA | NA |
| ADGRB2 | ADGRB1 | O60241 | 0.61 | −0.12 | −1.05 | 7 | NA | NA |
| PTPRN2 | PTPRN | Q92932 | 0.67 | −0.2 | −0.92 | 8 | NA | NA |
| GFRA2 | | O00451 | 0.8 | −0.12 | −0.98 | 9 | NA | NA |
| CBLN4 | CBLN1; CBLN3 | Q9NTU7 | 0.72 | −0.23 | −1.11 | 10 | NA | NA |
| HS6ST3 | | Q8IZP7 | 0.78 | −0.05 | −1.03 | 11 | NA | NA |
| PTPRN | | Q16849 | 0.59 | −0.19 | −1.05 | 12 | NA | NA |
| NRCAM | | Q92823 | 0.67 | 0.13 | −0.83 | 13 | NA | NA |
| LY6H | | O94772 | 0.55 | −0.07 | −0.89 | 14 | NA | NA |
| TMEM132D | TMEM132A; TMEM132C | Q14C87 | 0.76 | −0.17 | −0.94 | 15 | NA | NA |
| SCG2 | SCG3; SCG5 | P13521 | 0.53 | −0.04 | −1.06 | 16 | NA | NA |
| NELL2 | | Q99435 | 0.72 | 0.05 | −0.91 | 17 | NA | NA |
| BASP1 | | P80723 | 1.23 | 0.47 | −0.62 | 18 | NA | NA |
| PCSK1 | | P29120 | 0.56 | −0.25 | −1.08 | 19 | NA | NA |
| CRTAC1 | | Q9NQ79 | 0.73 | 0.1 | −0.89 | 20 | NA | NA |
| EPHA4 | EPHA5; EPHA7; EPHB6 | P54764 | 0.66 | 0.05 | −0.95 | 21 | NA | NA |
| CGREF1 | | Q99674 | 0.63 | −0.04 | −1.01 | 22 | NA | NA |
| CHL1 | | O00533 | 0.66 | 0.05 | −0.9 | 23 | NA | NA |
| GAP43 | | P17677 | 1.28 | 0.59 | −0.49 | 24 | NA | NA |
| FAIM2 | | Q9BWQ8 | 0.82 | 0.31 | −0.68 | 25 | NA | NA |
| OPCML | | Q14982 | 0.63 | 0.12 | −0.9 | 26 | NA | NA |
| CD99L2 | CD44; CD55; CD5L | Q8TCZ2 | 0.69 | 0.21 | −0.73 | 27 | NA | NA |
| FAM3C | | Q92520 | 0.63 | 0.21 | −0.8 | 28 | NA | NA |
| VSTM2B | | A6NLU5 | 0.48 | −0.12 | −1.05 | 29 | NA | NA |
| EPHA5 | | P54756 | 0.59 | −0.14 | −0.92 | 30 | NA | NA |
| THY1 | | P04216 | 0.67 | 0 | −0.99 | 31 | NA | NA |
| PRRT3 | | Q5FWE3 | 0.63 | 0 | −0.91 | 32 | NA | NA |
| GDA | | Q9Y2T3 | 1.36 | 0.64 | −0.27 | 33 | NA | NA |
| APLP1 | APLP2 | P51693 | 0.61 | 0.19 | −0.84 | 34 | NA | NA |
| CADM2 | | Q8N3J6 | 0.7 | 0.14 | −0.88 | 35 | NA | NA |
| CACNA2D3 | | Q8IZS8 | 0.79 | −0.01 | −0.76 | 36 | NA | NA |
| TNFRSF21 | | O75509 | 0.7 | 0.11 | −0.87 | 37 | NA | NA |
| LYNX1 | | P0DP58 | 0.6 | 0.11 | −0.87 | 38 | NA | NA |
| NPTX2 | | P47972 | 0.17 | −0.46 | −1.28 | 39 | NA | NA |
| SEZ6L | | Q9BYH1 | 0.7 | 0.07 | −0.89 | 40 | NA | NA |
| PAM | | P19021 | 0.55 | 0.06 | −0.98 | 41 | NA | NA |
| CNTN3 | | Q9P232 | 0.54 | −0.01 | −0.86 | 42 | NA | NA |
| TMEM132A | | Q24JP5 | 0.8 | 0.38 | −0.79 | 43 | NA | NA |
| CNTNAP2 | | Q9UHC6 | 0.64 | 0.13 | −0.83 | 44 | NA | NA |
| TGOLN2 | | O43493 | 0.6 | 0.2 | −0.86 | 45 | NA | NA |
| MAN2A2 | | P49641 | 0.62 | 0.09 | −0.92 | 46 | NA | NA |
| DCC | | P43146 | 0.48 | −0.18 | −0.99 | 47 | NA | NA |
| NPTXR | | O95502 | 0.38 | −0.2 | −1.16 | 48 | NA | NA |
| SCG3 | | Q8WXD2 | 0.5 | 0.11 | −0.93 | 49 | NA | NA |
| SLIT1 | | O75093 | 0.69 | 0.15 | −0.84 | 50 | NA | NA |
| EPHB6 | | O15197 | 0.65 | −0.07 | −0.66 | 51 | NA | NA |
| SEZ6L2 | | Q6UXD5 | 0.62 | 0.17 | −0.84 | 52 | NA | NA |
| PDGFB | PDGFA | P01127 | 0.63 | 0.11 | −0.84 | 53 | NA | NA |
| ICAM5 | | Q9UMF0 | 0.81 | 0.07 | −0.89 | 54 | NA | NA |
| IMPAD1 | | Q9NX62 | 0.52 | 0.26 | −0.86 | 55 | NA | NA |
| LDHB | | P07195 | 0.76 | 0.49 | −0.47 | 56 | NA | NA |
| CDH8 | | P55286 | 0.3 | −0.32 | −0.98 | 57 | NA | NA |
| RTN4RL2 | | Q86UN3 | 0.62 | −0.06 | −0.93 | 58 | NA | NA |
| NCAN | | O14594 | 0.71 | 0.16 | −0.83 | 59 | NA | NA |
| MDH1 | | P40925 | 1.28 | 0.78 | −0.47 | 60 | NA | NA |
| AJAP1 | | Q9UKB5 | 0.76 | 0.18 | −0.83 | 61 | NA | NA |
| CAMK2A | | Q9UQM7 | 1.12 | 0.48 | −0.46 | 62 | NA | NA |
| C4orf48 | | Q5BLP8 | 0.77 | 0.06 | −0.78 | 63 | NA | NA |
| CELSR2 | | Q9HCU4 | 0.7 | 0.04 | −0.87 | 64 | NA | NA |
| RGMB | | Q6NW40 | 0.63 | 0.18 | −0.89 | 65 | NA | NA |
| GOT1 | GOT2 | P17174 | 1.03 | 0.48 | −0.6 | 66 | NA | NA |

TABLE 2-continued

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| SUSD5 | | O60279 | 0.69 | 0.28 | −0.74 | 67 | NA | NA |
| LRP11 | | Q86VZ4 | 0.46 | 0.03 | −0.75 | 68 | NA | NA |
| NRXN3 | NRXN1; NRXN2; Q9P2S2 | Q9Y4C0 | 0.56 | 0.16 | −0.89 | 69 | NA | NA |
| EFNB2 | | P52799 | 0.56 | 0.22 | −0.86 | 70 | NA | NA |
| DDAH1 | | O94760 | 1.16 | 0.78 | −0.47 | 71 | NA | NA |
| SOD1 | SOD2 | P00441 | 0.85 | 0.38 | −0.62 | 72 | NA | NA |
| PRNP | | P04156 | 0.56 | 0.27 | −0.89 | 73 | NA | NA |
| IGSF21 | | Q96ID5 | 0.58 | 0.19 | −0.91 | 74 | NA | NA |
| SIRPB1 | O00241 | Q5TFQ8 | 0.47 | 0.15 | −0.88 | 75 | NA | NA |
| CSPG5 | | O95196 | 0.5 | −0.05 | −0.92 | 76 | NA | NA |
| LSAMP | | Q13449 | 0.65 | 0.23 | −0.81 | 77 | NA | NA |
| NCAM1 | NCAM2 | P13591 | 0.6 | 0.23 | −0.79 | 78 | NA | NA |
| PCDHGC5 | | Q9Y5F6 | 0.49 | −0.27 | −1.07 | 79 | NA | NA |
| CDH2 | | P19022 | 0.65 | 0.27 | −0.82 | 80 | NA | NA |
| NTM | | Q9P121 | 0.58 | 0.28 | −0.88 | 81 | NA | NA |
| PCDH1 | | Q08174 | 0.59 | 0.16 | −0.78 | 82 | NA | NA |
| ALDOA | ALDOC | P04075 | 1.31 | 0.76 | −0.5 | 83 | NA | NA |
| PTPRS | | Q13332 | 0.61 | 0.2 | −0.88 | 84 | NA | NA |
| ENDOD1 | | O94919 | 0.57 | 0.34 | −0.66 | 85 | NA | NA |
| LDHA | LDHB | P00338 | 0.91 | 0.63 | −0.38 | 86 | NA | NA |
| NAXE | | Q8NCW5 | 0.98 | 0.34 | −0.66 | 87 | NA | NA |
| GPR37 | | O15354 | 0.51 | 0.29 | −0.76 | 88 | NA | NA |
| EFNA3 | | P52797 | 0.67 | 0.21 | −0.85 | 89 | NA | NA |
| HSPA8 | | P11142 | 0.93 | 0.49 | −0.46 | 90 | NA | NA |
| BSG | | P35613 | 0.59 | 0.18 | −0.84 | 91 | NA | NA |
| ECM1 | | Q16610 | 0.47 | 0.08 | −0.65 | 92 | NA | NA |
| PKM | | P14618 | 1.27 | 0.82 | −0.31 | 93 | NA | NA |
| ALCAM | | Q13740 | 0.61 | 0.27 | −0.76 | 94 | NA | NA |
| IL6ST | | P40189 | 0.53 | 0.31 | −0.8 | 95 | NA | NA |
| OMG | | P23515 | 0.55 | 0.18 | −0.76 | 96 | NA | NA |
| MEGF9 | MEGF8; MEGF10 | Q9H1U4 | 0.54 | 0.12 | −0.93 | 97 | NA | NA |
| MANSC1 | | Q9H8J5 | 0.62 | 0.13 | −0.91 | 98 | NA | NA |
| ADGRB1 | | O14514 | 0.61) | 0.03 | −0.73 | 99 | NA | NA |
| PTPRD | | P23468 | 0.63 | 0.23 | −0.89 | 100 | NA | NA |
| UBA52 | | P62987 | 0.98 | 0.52 | −0.66 | 101 | NA | NA |
| RPS27A | | P62979 | 0.98 | 0.52 | −0.66 | 102 | NA | NA |
| UBB | UBC; UBA52; RPS27A | P0CG47 | 0.98 | 0.52 | −0.66 | 103 | NA | NA |
| UBC | | P63279 | 0.98 | 0.52 | −0.66 | 104 | NA | NA |
| PVR | | P15151 | 0.46 | 0.19 | −0.73 | 105 | NA | NA |
| SPP1 | | P10451 | 1.16 | 0.78 | −0.07 | 106 | NA | NA |
| CDH6 | | P55285 | 0.49 | 0.1 | −0.79 | 107 | NA | NA |
| SPARCL1 | | Q14515 | 0.56 | 0.24 | −0.76 | 108 | NA | NA |
| SORCS3 | | Q9UPU3 | 0.58 | 0.13 | −0.82 | 109 | NA | NA |
| NEGR1 | | Q7Z3B1 | 0.57 | 0.21 | −0.85 | 110 | NA | NA |
| CD55 | | P08174 | 0.53 | 0.24 | −0.81 | 111 | NA | NA |
| CST3 | CST6 | P01034 | 0.57 | 0.25 | −0.72 | 112 | NA | NA |
| EXTL2 | | Q9UBQ6 | 0.53 | 0.22 | −0.89 | 113 | NA | NA |
| NECTIN1 | | Q15223 | 0.39 | 0.09 | −0.74 | 114 | NA | NA |
| ST6GAL2 | | Q96JF0 | 0.48 | 0.17 | −0.98 | 115 | NA | NA |
| NPTX1 | NPTX2; NPTXR | Q15818 | 0.43 | 0.12 | −0.97 | 116 | NA | NA |
| ICOSLG | | O75144 | 0.5 | 0.15 | −0.8 | 117 | NA | NA |
| SCG5 | | P05408 | 0.58 | 0.28 | −0.94 | 118 | NA | NA |
| PIK3IP1 | | Q96FE7 | 0.56 | 0.29 | −0.75 | 119 | NA | NA |
| TXN | | P10599 | 0.96 | 0.57 | −0.41 | 120 | NA | NA |
| MT3 | | P25713 | 0.66 | 0.41 | −0.8 | 121 | NA | NA |
| NFASC | | O94856 | 0.58 | 0.26 | −0.82 | 122 | NA | NA |
| L1CAM | | P32004 | 0.67 | 0.37 | −0.82 | 123 | NA | NA |
| SERPINI1 | | Q99574 | 0.51 | 0.15 | −0.8 | 124 | NA | NA |
| SEMA4B | | Q9NPR2 | 0.55 | 0.4 | −0.75 | 125 | NA | NA |
| NRXN1 | | Q9ULB1 | 0.57 | 0.3 | −0.87 | 126 | NA | NA |
| PCSK1N | PCSK1; PCSK2 | Q9UHG2 | 0.6 | 0.32 | −0.81 | 127 | NA | NA |
| PTPRG | | P23470 | 0.53 | 0.24 | −0.84 | 128 | NA | NA |
| SLC39A10 | Q9HBR0 | Q9ULF5 | 0.68 | 0.15 | −0.8 | 129 | NA | NA |
| LRRC4 | | Q9HBW1 | 0.6 | 0.43 | −0.63 | 130 | NA | NA |
| NRN1 | | Q9NPD7 | 0.56 | 0.15 | −0.88 | 131 | NA | NA |
| NEO1 | | Q92859 | 0.59 | 0.3 | −0.87 | 132 | NA | NA |
| DKK3 | | Q9UBP4 | 0.48 | 0.19 | −0.72 | 133 | NA | NA |
| B4GAT1 | | O43505 | 0.59 | 0.3 | −0.8 | 134 | NA | NA |
| SORCS2 | SORCS1; SORCS3; SORT1 | Q96PQ0 | 0.72 | 0.5 | −0.5 | 135 | NA | NA |
| LINGO1 | | Q96FE5 | 0.54 | 0.14 | −0.8 | 136 | NA | NA |
| CHRD | | Q9H2X0 | 0.66 | 0.31 | −0.84 | 137 | NA | NA |
| NCAM2 | | O15394 | 0.57 | 0.23 | −0.72 | 138 | NA | NA |
| APP | | P05067 | 0.57 | 0.32 | −0.83 | 139 | NA | NA |
| CADM3 | | Q8N126 | 0.49 | 0.28 | −0.85 | 140 | NA | NA |

TABLE 2-continued

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| ALDOC | | P09972 | 0.82 | 0.5 | −0.67 | 141 | NA | NA |
| SIRPG | | Q9P1W8 | 0.34 | 0.11 | −0.64 | 142 | NA | NA |
| DNER | | Q8NFT8 | 0.39 | 0.25 | −0.77 | 143 | NA | NA |
| PCDH10 | | Q9P2E7 | 0.61 | 0.13 | −0.71 | 144 | NA | NA |
| FGFR3 | | P22607 | 0.55 | 0.12 | −0.83 | 145 | NA | NA |
| SIRPA | | P78324 | 0.35 | 0.14 | −0.77 | 146 | NA | NA |
| HYOU1 | | Q9Y4L1 | 0.49 | 0.25 | −0.88 | 147 | NA | NA |
| RGMA | | Q96B86 | 0.5 | 0.2 | −0.59 | 148 | NA | NA |
| CYCS | | P99999 | 0.78 | 0.37 | −0.74 | 149 | NA | NA |
| LAMP2 | LAMP1 | P13473 | 0.64 | 0.37 | −0.65 | 150 | NA | NA |
| POMGNT1 | | Q8WZA1 | 0.57 | 0.14 | −0.75 | 151 | NA | NA |
| LRRC4B | | Q9NT99 | 0.58 | 0.36 | −0.76 | 152 | NA | NA |
| PEBP1 | PEBP4 | P30086 | 0.95 | 0.65 | −0.48 | 153 | NA | NA |
| SIRPB1 | | O00241 | 0.34 | 0.14 | −0.68 | 154 | NA | NA |
| PTPRF | | P10586 | 0.81 | 0.2 | −0.85 | 155 | NA | NA |
| CANX | | P27824 | 0.5 | 0.4 | −0.51 | 156 | NA | NA |
| ATP6AP1 | | Q15904 | 0.45 | 0.23 | −0.88 | 157 | NA | NA |
| CANT1 | | Q8WVQ1 | 0.55 | 0.29 | −0.78 | 158 | NA | NA |
| FAM19A5 | | Q7Z5A7 | 0.6 | 0.39 | −0.83 | 159 | NA | NA |
| MEGF8 | | Q7Z7M0 | 0.51 | 0.27 | −0.8 | 160 | NA | NA |
| PRKCSH | | P14314 | 0.6 | 0.31 | −0.83 | 161 | NA | NA |
| CLSTN1 | CLSTN3 | O94985 | 0.63 | 0.36 | −0.83 | 162 | NA | NA |
| ADGRL1 | | O94910 | 0.45 | 0.16 | −0.93 | 163 | NA | NA |
| GOT2 | | P00505 | 0.8 | 0.55 | −0.56 | 164 | NA | NA |
| EFCAB14 | | O75071 | 0.36 | 0.18 | −0.8 | 165 | NA | NA |
| CARTPT | | Q16568 | 0.31 | 0.08 | −0.45 | 166 | NA | NA |
| CHST10 | | O43529 | 0.51 | 0.02 | −0.76 | 167 | NA | NA |
| TPI1 | | P60174 | 0.83 | 0.58 | −0.67 | 168 | NA | NA |
| LMAN2 | | Q12907 | 0.53 | 0.32 | −0.71 | 169 | NA | NA |
| PCDHAC2 | | Q9Y5I4 | 0.41 | 0.26 | −0.93 | 170 | NA | NA |
| FAM198B | | Q6UWH4 | 0.53 | 0.34 | −0.59 | 171 | NA | NA |
| ART3 | | Q13508 | 0.57 | 0.41 | −0.54 | 172 | NA | NA |
| EPHA7 | | Q15375 | 0.41 | 0.25 | −0.67 | 173 | NA | NA |
| MEGF10 | | Q96KG7 | 0.65 | 0.31 | −0.7 | 174 | NA | NA |
| PCDH17 | | O14917 | 0.43 | 0.19 | −0.8 | 175 | NA | NA |
| PCDH9 | | Q9HC56 | 0.51 | 0.28 | −0.82 | 176 | NA | NA |
| MASP1 | | P48740 | 0.11 | 0.85 | −0.45 | NA | 1 | NA |
| F5 | F2; F9 | P12259 | −0.33 | 0.58 | −0.5 | NA | 2 | NA |
| CTSD | | P07339 | −0.07 | 0.75 | −0.49 | NA | 3 | NA |
| DCN | | P07585 | −0.31 | 0.63 | −0.57 | NA | 4 | NA |
| RNASE4 | RNASE1; RNASE6; RNASET2 | P3409S | 0.01 | 0.72 | −0.11 | NA | 5 | NA |
| HTRA1 | | Q92743 | 0.41 | 0.84 | −0.5 | NA | 6 | NA |
| LTBP2 | | Q14767 | 0.06 | 0.85 | −0.21 | NA | 7 | NA |
| PROS1 | | P07225 | −0.2 | 0.67 | 0.02 | NA | 8 | NA |
| LTBP1 | LTBP2 | Q14766 | 0.19 | 0.78 | −0.53 | NA | 9 | NA |
| IGFBP7 | IGFBP2; IGFBP4; IGFBP6 | Q16270 | −0.33 | 0.46 | −0.52 | NA | 10 | NA |
| OLFML3 | OLFM1 | Q9NRN5 | 0.13 | 0.62 | −0.6 | NA | 11 | NA |
| COL18A1 | COL6A1; COL6A3 | P39060 | 0.27 | 0.59 | −0.61 | NA | 12 | NA |
| ECM2 | ECM1 | O94769 | 0.01 | 0.68 | −0.25 | NA | 13 | NA |
| C1S | C1R; C1RL; C1QA; C1QC; C2; C3; C4A; C4B; | P09871 | 0.23 | 0.56 | −0.62 | NA | 14 | NA |
| CTBS | | Q01459 | 0.09 | 0.57 | −0.49 | NA | 15 | NA |
| FMOD | | Q06828 | −0.14 | 0.6 | −0.22 | NA | 16 | NA |
| FRZB | | Q92765 | 0.25 | 0.78 | −0.32 | NA | 17 | NA |
| LAMB1 | | P07942 | −0.08 | 0.51 | −0.81 | NA | 18 | NA |
| IGFBP2 | | P18065 | 0.14 | 0.73 | −0.46 | NA | 19 | NA |
| MAN1C1 | MAN1A1 | Q9NR34 | 0.11 | 0.66 | −0.64 | NA | 20 | NA |
| COL6A3 | | P12111 | 0.1 | 0.66 | −0.33 | NA | 21 | NA |
| MSTN | | O14793 | 0 | 0.18 | −0.81 | NA | 22 | NA |
| C1R | | P00736 | 0.25 | 0.58 | −0.53 | NA | 23 | NA |
| OMD | | Q99983 | 0.15 | 0.69 | −0.31 | NA | 24 | NA |
| PLTP | | P55058 | 0.1 | 0.55 | −0.32 | NA | 25 | NA |
| TTR | | P02766 | −0.32 | 0.52 | −0.29 | NA | 26 | NA |
| PCOLCE | | Q15113 | 0.18 | 0.59 | −0.48 | NA | 27 | NA |
| SORT1 | SORCS1; SORCS3 | Q99523 | 0.27 | 0.63 | −0.52 | NA | 28 | NA |
| FBLN2 | FBLN5 | P98095 | 0.26 | 0.59 | −0.64 | NA | 29 | NA |
| PTN | | P21246 | 0.15 | 0.61 | −0.51 | NA | 30 | NA |
| RNASET2 | | O00584 | 0.33 | 0.63 | −0.47 | NA | 31 | NA |
| SPOCK1 | SPOCK2; SPOCK3 | Q08629 | 0.34 | 0.56 | −0.75 | NA | 32 | NA |
| LGALS1 | | P09382 | 0.25 | 0.62 | −0.37 | NA | 33 | NA |
| SPOCK3 | | Q9BQ16 | 0.33 | 0.47 | −0.58 | NA | 34 | NA |
| CTSB | CTBS; CTSD; CTSS; CTGF | P07858 | 0.32 | 0.54 | −0.56 | NA | 35 | NA |
| NOV | | P48745 | 0.09 | 0.34 | −0.67 | NA | 36 | NA |
| COL6A1 | | P12109 | 0.35 | 0.52 | −0.79 | NA | 37 | NA |

TABLE 2-continued

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| PLXNB2 | | O15031 | 0.24 | 0.48 | −0.71 | NA | 38 | NA |
| FBLN5 | | Q9UBX5 | 0.38 | 0.82 | −0.61 | NA | 39 | NA |
| GALNT2 | | Q10471 | 0.38 | 0.49 | −0.72 | NA | 40 | NA |
| MMP11 | MMP2 | P24347 | 0.07 | 0.66 | −0.3 | NA | 41 | NA |
| MCAM | | P43121 | 0.3 | 0.49 | −0.77 | NA | 42 | NA |
| SELENOP | | P49908 | 0.12 | 0.42 | −0.18 | NA | 43 | NA |
| LRP1 | | Q07954 | 0.5 | 0.62 | −0.62 | NA | 44 | NA |
| FSTL5 | | Q8N475 | 0.05 | 0.37 | −0.75 | NA | 45 | NA |
| CNTN2 | | Q02246 | 0.22 | 0.47 | −0.56 | NA | 46 | NA |
| GALNT10 | GALNT2; GALNT7; GALNT18 | Q86SR1 | 0.26 | 0.52 | −0.42 | NA | 47 | NA |
| HSPG2 | | P98160 | 0.33 | 0.61 | −0.36 | NA | 48 | NA |
| SEMA3B | SEMA3G | Q13214 | 0.08 | 0.5 | −0.25 | NA | 49 | NA |
| ITM2B | | Q9Y287 | 0.34 | 0.46 | −0.58 | NA | 50 | NA |
| SLPI | | P03973 | −0.12 | 0.63 | 0.08 | NA | 51 | NA |
| VCAN | | P13611 | 0.36 | 0.48 | −0.62 | NA | 52 | NA |
| FAT2 | | Q9NYQ8 | 0.06 | 0.46 | −0.84 | NA | 53 | NA |
| MMP2 | | P08253 | 0.04 | 0.61 | −0.39 | NA | 54 | NA |
| GOLM1 | | Q8NBJ4 | 0.38 | 0.33 | −0.81 | NA | 55 | NA |
| SPOCK2 | | Q92563 | 0.47 | 0.54 | −0.77 | NA | 56 | NA |
| PPIC | | P45877 | 0.37 | 0.45 | −0.61 | NA | 57 | NA |
| RNASE6 | | Q93091 | 0.53 | 0.65 | −0.47 | NA | 58 | NA |
| PSAP | | P07602 | 0.45 | 0.47 | −0.7 | NA | 59 | NA |
| RELN | | P78509 | −0.01 | 0.32 | −0.8 | NA | 60 | NA |
| TGFBI | | Q15582 | 0.16 | 0.64 | −0.34 | NA | 61 | NA |
| KIT | | P10721 | 0.07 | 0.37 | −0.91 | NA | 62 | NA |
| C1QB | C1QA; C1QC | P02746 | 0.28 | 0.54 | −0.58 | NA | 63 | NA |
| CD44 | | P16070 | 0.62 | 0.69 | −0.37 | NA | 64 | NA |
| SPON1 | | Q9HCB6 | 0.74 | 0.7 | −0.62 | NA | 65 | NA |
| EFEMP1 | | Q12805 | 0.6 | 0.7 | −0.39 | NA | 66 | NA |
| LAMA2 | | P24043 | −0.02 | 0.53 | −0.68 | NA | 67 | NA |
| CBLN3 | | Q6UW01 | 0.09 | 0.4 | −0.86 | NA | 68 | NA |
| CBLN1 | | P23435 | 0.17 | 0.45 | −0.81 | NA | 69 | NA |
| TNXA | | P22105 | −0.21 | 0.26 | −0.63 | NA | 70 | NA |
| MOG | | Q16653 | 0.51 | 0.56 | −0.63 | NA | 71 | NA |
| CDH15 | | P55291 | −0.07 | 0.31 | −0.72 | NA | 72 | NA |
| CLU | | P10909 | 0.27 | 0.53 | −0.53 | NA | 73 | NA |
| C1QA | | P02745 | 0.34 | 0.5 | −0.49 | NA | 74 | NA |
| NPC2 | | P61916 | 0.47 | 0.63 | −0.55 | NA | 75 | NA |
| APOE | | P02649 | 0.3 | 0.3 | −0.89 | NA | 76 | NA |
| FGFR1 | FGFR2; FGFR3 | P11362 | 0.29 | 0.33 | −0.88 | NA | 77 | NA |
| NSG1 | | P42857 | 0.41 | 0.35 | −0.77 | NA | 78 | NA |
| GANAB | | Q14697 | 0.21 | 0.21 | −1.08 | NA | 79 | NA |
| LAMB2 | LAMB1 | P55268 | 0.26 | 0.45 | −0.65 | NA | 80 | NA |
| CSF1 | | P09603 | 0.58 | 0.64 | −0.56 | NA | 81 | NA |
| CNTN1 | CNTN2; CNTN3; CNTN4; CNTN6 | Q12860 | 0.45 | 0.4 | −0.68 | NA | 82 | NA |
| CHAD | | O15335 | 0.07 | 0.39 | −0.83 | NA | 83 | NA |
| TNR | | Q92752 | 0.39 | 0.42 | −0.85 | NA | 84 | NA |
| PTPRZ1 | | P23471 | 0.49 | 0.47 | −0.72 | NA | 85 | NA |
| GAA | | P10253 | 0.44 | 0.36 | −0.52 | NA | 86 | NA |
| NXPH4 | | O95158 | 0.19 | 0.39 | −0.79 | NA | 87 | NA |
| SGCE | | O43556 | 0.44 | 0.45 | −0.8 | NA | 88 | NA |
| SEZ6 | SEZ6L; SEZ6L2 | Q53EL9 | 0.35 | 0.35 | −0.85 | NA | 89 | NA |
| NPPC | | P23582 | 0.36 | 0.36 | −0.81 | NA | 90 | NA |
| MSN | | P26038 | 0.36 | 0.61 | −0.37 | NA | 91 | NA |
| CTSS | | P25774 | 0.49 | 0.67 | −0.36 | NA | 92 | NA |
| PVALB | | P20472 | 0.48 | 0.56 | −0.51 | NA | 93 | NA |
| PHLDB3 | | Q6NSJ2 | 0.39 | 0.46 | −0.59 | NA | 94 | NA |
| PDIA3 | | P30101 | 0.54 | 0.57 | −0.85 | NA | 95 | NA |
| C16orf89 | | Q6UX73 | 0.37 | 0.47 | −0.57 | NA | 96 | NA |
| PLG | PLGLA; PLGLB1 | P00747 | −0.65 | −0.5 | 0.74 | NA | NA | 1 |
| KNG1 | | P01042 | −0.73 | −0.62 | 0.51 | NA | NA | 2 |
| SERPINF2 | | P08697 | −0.69 | −0.49 | 0.56 | NA | NA | 3 |
| AFM | | P43652 | −0.55 | −0.5 | 0.62 | NA | NA | 4 |
| ALB | | P02768 | −0.68 | −0.29 | 0.77 | NA | NA | 5 |
| C8A | C8B; C6; C9 | P07357 | −0.38 | −0.32 | 0.71 | NA | NA | 6 |
| HABP2 | | Q14520 | −0.57 | −0.54 | 0.62 | NA | NA | 7 |
| GC | | P02774 | −0.63 | −0.3 | 0.82 | NA | NA | 8 |
| SERPINC1 | | P01008 | −0.56 | −0.25 | 0.79 | NA | NA | 9 |
| C8B | | P07358 | −0.3 | −0.31 | 0.68 | NA | NA | 10 |
| APOA2 | | P02652 | −0.45 | −0.53 | 0.66 | NA | NA | 11 |
| APOA1 | APOA2 | P02647 | −0.52 | −0.44 | 0.75 | NA | NA | 12 |
| SERPINA6 | | P08185 | −0.44 | −0.17 | 0.7 | NA | NA | 13 |

TABLE 2-continued

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| SERPINA4 | SERPINA1; SERPINA3; SERPINA6; SERPINA7 | P29622 | −0.7 | −0.49 | 0.64 | NA | NA | 14 |
| A1BG | | P04217 | −0.35) | −0.37 | 0.73 | NA | NA | 15 |
| CFB | | P00751 | −0.65 | −0.45 | 0.44 | NA | NA | 16 |
| F2 | | P00734 | −0.49 | −0.32 | 0.71 | NA | NA | 17 |
| HPX | | P02790 | −0.77 | −0.31 | 0.82 | NA | NA | 18 |
| CPB2 | | Q96IY4 | −0.66 | −0.45 | 0.56 | NA | NA | 19 |
| SERPINA7 | | P05543 | −0.64 | −0.21 | 0.94 | NA | NA | 20 |
| IGKV3D-11 | | A0A0A0MRZ8 | −0.59 | −0.42 | 0.31 | NA | NA | 21 |
| IGKV3-11 | IGKV3-20 | P04433 | −0.59 | −0.42 | 0.31 | NA | NA | 22 |
| APOH | | P02749 | −0.54 | −0.34 | 0.49 | NA | NA | 23 |
| APOM | | O95445 | −0.38 | −0.41 | 0.74 | NA | NA | 24 |
| PLGLA | | Q15195 | −0.55 | −0.31 | 0.49 | NA | NA | 25 |
| C6 | | P13671 | −0.24 | −0.28 | 0.75 | NA | NA | 26 |
| PON1 | | P27169 | −0.46 | −0.49 | 0.49 | NA | NA | 27 |
| PLGLB1 | | Q02325 | −0.68 | −0.53 | 0.79 | NA | NA | 28 |
| SAA4 | | P35542 | −0.17 | −0.36 | 0.67 | NA | NA | 29 |
| VTN | | P04004 | −0.67 | −0.54 | 0.46 | NA | NA | 30 |
| F12 | | P00748 | −0.4 | −0.36 | 0.49 | NA | NA | 31 |
| CFI | | P05156 | −0.68 | −0.5 | 0.54 | NA | NA | 32 |
| MST1 | MST1L | P26927 | −0.32 | −0.31 | 0.42 | NA | NA | 33 |
| IGKV3-20 | | P01619; A0A0C4DH25 | −0.61 | −0.44 | 0.29 | NA | NA | 34 |
| IGHV3-7 | | P01780 | −0.56 | −0.5 | 0.28 | NA | NA | 35 |
| MST1L | | Q2TV78 | −0.3 | −0.22 | 0.46 | NA | NA | 36 |
| P0DOX7 | | P0DOX7 | −0.57 | −0.45 | 0.57 | NA | NA | 37 |
| IGLC3 | | P0DOY3 | −0.5 | −0.45 | 0.44 | NA | NA | 38 |
| IGLC2 | IGLC3 | P0DOY2; P0DOX8 | −0.5 | −0.45 | 0.44 | NA | NA | 39 |
| AZGP1 | | P25311 | −0.43 | 0.01 | 0.68 | NA | NA | 40 |
| IGHG3 | | P01860 | −0.42 | −0.5 | 0.42 | NA | NA | 41 |
| UACA | | Q9BZF9 | −0.56 | −0.49 | 0.47 | NA | NA | 42 |
| P0DOX5 | | PODOX5 | −0.46 | −0.35 | 0.5 | NA | NA | 43 |
| IGFALS | | P35858 | −0.6 | −0.47 | 0.44 | NA | NA | 44 |
| IGHG1 | IGHG3 | P01857 | −0.46 | −0.34 | 0.5 | NA | NA | 45 |
| IGHV3-72 | | A0A0B4J1Y9 | −0.58 | −0.42 | 0.42 | NA | NA | 46 |
| KLKB1 | | P03952 | −0.52 | −0.55 | 0.54 | NA | NA | 47 |
| SERPINA1 | | P01009 | −0.46 | −0.17 | 0.84 | NA | NA | 48 |
| IGKC | | P01834; P0DOX7 | −0.58 | −0.48 | 0.5 | NA | NA | 49 |
| FETUB | | Q9UGM5 | −0.51 | −0.67 | 0.51 | NA | NA | 50 |
| C2 | | P06681 | −0.48 | −0.26 | 0.31 | NA | NA | 51 |
| GPLD1 | | P80108 | −0.91 | −0.87 | 0.1 | NA | NA | 52 |
| APCS | | P02743 | −0.56 | −0.67 | 0.29 | NA | NA | 53 |
| CP | | P00450 | −0.35 | −0.13 | 0.74 | NA | NA | 54 |
| IGHV1-2 | | P23083 | −0.49 | −0.37 | 0.33 | NA | NA | 55 |
| C9 | | P02748 | −0.21 | −0.2 | 0.78 | NA | NA | 56 |
| F9 | | P00740 | −0.44 | −0.16 | 0.64 | NA | NA | 57 |
| IGKV2D-29 | | A0A075B6S2 | −0.55 | −0.45 | 0.45 | NA | NA | 58 |
| IGKV2-29 | | A2NJV5 | −0.55 | −0.45 | 0.45 | NA | NA | 59 |
| IGKV2D-26 | IGKV2D-29; IGKV2D-30 | A0A0A0MRZ7 | −0.54 | −0.45 | 0.43 | NA | NA | 60 |
| P0DOX2 | | P0DOX2 | −0.33 | −0.4 | 0.42 | NA | NA | 61 |
| ITIH3 | | Q06033 | −0.16 | −0.06 | 0.81 | NA | NA | 62 |
| IGKV1-5 | | P01602 | −0.25 | −0.27 | 0.23 | NA | NA | 63 |
| APOL1 | | O14791 | −0.43 | −0.58 | 0.53 | NA | NA | 64 |
| ORM1 | | P02763 | −0.28 | −0.32 | 0.65 | NA | NA | 65 |
| C1RL | | Q9NZP8 | −0.2 | −0.28 | 0.3 | NA | NA | 66 |
| IGHV4-61 | | A0A0C4DH41 | −0.33 | −0.23 | 0.38 | NA | NA | 67 |
| IGKV2D-30 | | A0A075B6S6 | −0.54 | −0.46 | 0.41 | NA | NA | 68 |
| IGHV4-30-4 | IGHV4-34; IGHV4-38-2; IGHV4-39; IGHV4-59; IGHV4-61 | P0DP06 | −0.33 | −0.23 | 0.38 | NA | NA | 69 |
| IGHV4-59 | | P08125 | −0.33 | −0.23 | 0.38 | NA | NA | 70 |
| IGHV4-38-2 | | P0DP08 | −0.33 | −0.23 | 0.38 | NA | NA | 71 |
| IGHV4-39 | | P01824 | −0.33 | −0.23 | 0.38 | NA | NA | 72 |
| IGHV4-34 | | P06331; A0A087WSY4; A0A075B6R2 | −0.33 | −0.23 | 0.38 | NA | NA | 73 |
| IGHV3-64D | | A0A0J9YX35 | −0.41 | −0.42 | 0.24 | NA | NA | 74 |
| OPTN | | Q96CV9 | −0.42 | 0 | 0.47 | NA | NA | 75 |
| LRG1 | | P02750 | −0.18 | 0.04 | 0.74 | NA | NA | 76 |
| IGKV2-24 | IGKV2-29 | A0A0C4DH68 | −0.43 | −0.33 | 0.21 | NA | NA | 77 |
| C4B | | P0C0L5 | 0.14 | −0.15 | 0.26 | NA | NA | 78 |
| IGHV3-30 | IGHV3-43D; IGHV3-64D; IGHV3-7; IGHV3-72; IGHV3-9 | P01768; P01764 | −0.61 | −0.61 | 0.32 | NA | NA | 79 |
| LUM | | P51884 | −0.59 | 0.33 | 0.55 | NA | NA | 80 |
| CFHR2 | | P36980 | −0.21 | −0.11 | 0.48 | NA | NA | 81 |
| IGLV9-49 | | A0A0B4J1Y8 | −0.37 | −0.41 | 0.29 | NA | NA | 82 |

TABLE 2-continued

Overview of gene expression products that help in identifying Subtype 1, Subtype 2, and Subtype 3 patients. Included in columns 4-6 are the average protein concentrations for each subtype, values are Z-transformed according to the mean and standard deviation of a control group.

| Gene name | Related prroteins | Uniprot | Subtype 1 | Subtype 2 | Subtype 3 | S1.ranking | S2.ranking | S3.ranking |
|---|---|---|---|---|---|---|---|---|
| F13B | | P05160 | −0.65 | −0.36 | 0.5 | NA | NA | 83 |
| IGLV3-10 | | A0A075B6K4 | −0.48 | −0.27 | 0.34 | NA | NA | 84 |
| APOC1 | APOC2 | P02654 | −0.25 | −0.35 | 0.36 | NA | NA | 85 |
| SERPINA3 | | P01011 | −0.04 | 0.14 | 0.74 | NA | NA | 86 |
| CD5L | | O43866 | −0.38 | −0.4 | 0.34 | NA | NA | 87 |
| APOC2 | | P02655 | −0.21 | −0.25 | 0.27 | NA | NA | 88 |
| TF | | P02787 | −0.35 | −0.34 | 0.08 | NA | NA | 89 |
| IGHM | | P01871 | −0.42 | −0.46 | 0.26 | NA | NA | 90 |
| IGHV3-43D | | P0DP04 | −0.68 | −0.46 | 0.19 | NA | NA | 91 |
| IGHV3-9 | | P01782 | −0.68 | −0.46 | 0.19 | NA | NA | 92 |
| IL1RAP | | Q9NPH3 | −0.1 | 0.23 | 0.31 | NA | NA | 93 |
| METTL18 | | O95568 | −0.44 | −0.24 | 0.01 | NA | NA | 94 |
| APOD | | P05090 | 0.03 | 0.45 | 0.29 | NA | NA | 95 |
| IGFBP6 | | P24592 | −0.13 | 0.23 | −0.06 | NA | NA | 96 |
| C4A | | P0C0L4 | 0.21 | 0.3 | 0.09 | NA | NA | 97 |

TABLE 3

Percentage correct (95% CI) subtype prediction for different number of proteins.

| Number of proteins | Subtype 1 | Subtype 2 | Subtype 3 | Overall |
|---|---|---|---|---|
| Top 3 | 72.7 (58.2, 89.2) | 67.7 (47.8, 89.2) | 79.2 (60.9, 94.9) | 72.9 (63.4, 82.1) |
| Top 6 | 78.4 (60.8, 95.8) | 70.3 (51, 88.9) | 80.8 (65.4, 95.5) | 76.5 (67.2, 85.1) |
| Top 9 | 80 (62.1, 95.1) | 72.1 (52.5, 89.2) | 82.5 (66, 96) | 78 (68.7, 85.1) |
| Top 15 | 81.4 (65.2, 96) | 76.2 (56.2, 94.3) | 82.9 (67.2, 100) | 80 (71.6, 88.1) |
| Top 30 | 83 (66.7, 96.2) | 79.2 (59.6, 94.7) | 86.4 (72.1, 100) | 82.6 (74.6, 89.6) |
| Top 45 | 83.5 (65.5, 100) | 79.1 (63.2, 94.7) | 87.6 (71.4, 100) | 83.3 (74.6, 91) |
| Top 60 | 84.5 (67.2, 100) | 82.9 (62.2, 100) | 88.2 (70.8, 100) | 85 (76.1, 92.5) |
| Top 75 | 85.8 (68.1, 100) | 82.6 (63.2, 100) | 87.2 (69.4, 100) | 85 (76.1, 92.5) |
| Top 90 | 84.7 (66.7, 100) | 83.1 (65, 100) | 88.1 (70.8, 100) | 85.1 (77.6, 92.5) |
| Top 102 | 84.3 (69.1, 96.2) | 82.6 (60, 100) | 88.3 (71.7, 100) | 84.8 (76.1, 92.5) |
| All 369 proteins | 82.9 (61.9, 100) | 78.1 (55.3, 95.4) | 89.2 (75, 100) | 83.3 (73.1, 92.5) |

TABLE 4

DICE overlap of AD and controls for proteins that differ between subtypes.

| | EMIF-AD MBD number of proteins | | | | ADNI number of proteins | | | |
|---|---|---|---|---|---|---|---|---|
| Contrast | Control | AD | Overlap | DICE | Control | AD | Overlap | DICE |
| Subtype 1 > Subtype 3 | 427 | 434 | 415 | 0.96 | 79 | 130 | 77 | 0.74 |
| Subtype 1 > Subtype 2 | 39 | 166 | 8 | 0.08 | 84 | 78 | 65 | 0.8 |
| Subtype 2 > Subtype 1 | 74 | 67 | 15 | 0.21 | 2 | 15 | 0 | 0 |
| Subtype 2 > Subtype 3 | 447 | 448 | 442 | 0.99 | 23 | 129 | 21 | 0.28 |
| Subtype 3 > Subtype 1 | 91 | 93 | 89 | 0.97 | 3 | 3 | 0 | 0 |
| Subtype 3 > Subtype 2 | 88 | 91 | 87 | 0.97 | 21 | 3 | 0 | 0 |

TABLE 5

Proteins for potential subgroup 4: Indicated are the proteins that differ 100% from the other 3 subtypes.

| Gene name | Related proteins | Overlap with table 2 | Uniprot | Subtype 1 | Subtype 2 | Subtype 3 | Subtype 4 |
|---|---|---|---|---|---|---|---|
| ACTB | ACTG1 | | P60709 | 0.17 | 0.16 | 0.16 | −3.75 |
| ACTBL2 | | | Q562R1 | 0.15 | 0.18 | 0.21 | −4.04 |
| ACTG1 | | | P63261 | 0.17 | 0.16 | 0.16 | −3.75 |
| BTD | | | P42351 | −0.04 | 0.04 | 0.21 | 2.49 |
| C2 | | Subtype 3 | P06681 | −0.07 | −0.23 | −0.18 | 2.81 |
| COL6A3 | | Subtype 2 | P12111 | −0.01 | 0.16 | 0.28 | 2.84 |

TABLE 5-continued

Proteins for potential subgroup 4: Indicated are the proteins that differ 100% from the other 3 subtypes.

| Gene name | Related proteins | Overlap with table 2 | Uniprot | Subtype 1 | Subtype 2 | Subtype 3 | Subtype 4 |
|---|---|---|---|---|---|---|---|
| ENO1 | | | P06733 | 0.49 | 0.48 | 0.57 | −3.57 |
| MINPP1 | | | Q9UNW1 | −0.06 | 0.02 | 0.15 | 2.69 |
| MSTN | | Subtype 2 | O14793 | −0.23 | −0.26 | −0.12 | 2.55 |
| NOV | | Subtype 2 | P48745 | −0.09 | −0.08 | −0.05 | 2.22 |
| NRP2 | | | O60462 | −0.17 | −0.22 | 0.07 | 2.76 |
| PLTP | | Subtype 2 | P55058 | −0.02 | 0.24 | 0.12 | 2.74 |
| POTEE | | | Q6S8J3 | 0.2 | 0.16 | 0.17 | −4.21 |
| POTEF | | | A5A3E0 | 0.2 | 0.16 | 0.17 | −4.21 |
| POTEKP | | | Q9BYX7 | 0.2 | 0.12 | 0.15 | −4.65 |
| PRDX1 | PRDX4; PRDX6 | | Q06830 | 0.24 | 0.32 | 0.26 | −3.76 |
| PRDX4 | | | Q13162 | 0.24 | 0.34 | 0.29 | −4.09 |
| PRDX6 | | | P30041 | 0.16 | 0.18 | 0.1 | −2.4 |
| PROS1 | | Subtype 2 | P07225 | 0.09 | 0.17 | 0.19 | 3.63 |
| SELENOP | | Subtype 2 | P49908 | 0.01 | 0.17 | 0.19 | 3.51 |
| TGFBR3 | | | Q03167 | −0.14 | −0.07 | 0.08 | 3.24 |
| TPM1 | TPM2 | | P09493 | 0.13 | 0.13 | 0.12 | −3.93 |
| TPM2 | | | P07951 | 0.14 | 0.13 | 0.13 | −3.86 |
| YWHAE | YWHAZ | | P62258 | 0.79 | 0.92 | 0.85 | −3.07 |
| YWHAZ | | | P63104 | 0.82 | 0.82 | 0.83 | −4.07 |

TABLE 6

Proportions or estimated marginal means (se) for biomarker comparisons. EMIF-AD Total Alzheimer's disease sample

| Variable | n missing | S 1 | S 1 se | S 2 | S 2 se | S 3 | S 3 se | p value S 1 vs S 2 | p value S 1 vs 3 | p value S 2 vs S3 |
|---|---|---|---|---|---|---|---|---|---|---|
| Disease stage: | | | | | | | | | | |
| Normal cognition, n (%) | 0 | 19 (24%) | n.a. | 18 (25%) | n.a. | 19 (26%) | n.a. | 1 | 0.851 | 1 |
| MCI, n (%) | 0 | 37 (46%) | n.a. | 27 (38%) | n.a. | 26 (36%) | n.a. | 0.392 | 0.27 | 0.949 |
| Dementia, n (%) | 0 | 24 (30%) | n.a. | 26 (37%) | n.a. | 27 (38%) | n.a. | 0.491 | 0.42 | 1 |
| Female, n (%) | 0 | 50 (63%) | n.a. | 44 (62%) | n.a. | 30 (42%) | n.a. | 1 | 0.016 | 0.024 |
| APOE e4 carrier, n (%) | 0 | 53 (71%) | n.a. | 40 (61%) | n.a. | 45 (67%) | n.a. | 0.28 | 0.788 | 0.544 |
| Age | 0 | 68.51 | 0.898 | 67.48 | 0.933 | 67.72 | 0.922 | 0.429 | 0.539 | 0.859 |
| T-tau | 1 | 7.298 | 0.472 | 3.261 | 0.498 | 2.195 | 0.494 | 1.453E−08 | 1.877E−12 | 0.130 |
| P-tau | 0 | 3.563 | 0.246 | 1.405 | 0.261 | 1.057 | 0.259 | 7.444E−09 | 2.862E−11 | 0.345 |
| Abeta 1-40 | 0 | 1.139 | 0.140 | −0.237 | 0.149 | −0.400 | 0.148 | 1.385E−10 | 1.068E−12 | 0.439 |
| Abeta 1-38 | 1 | 1.279 | 0.141 | −0.301 | 0.150 | −0.520 | 0.148 | 5.533E−13 | 4.175E−16 | 0.301 |
| Neurogranin | 15 | 1.461 | 0.141 | 0.093 | 0.154 | −0.019 | 0.158 | 4.358E−10 | 3.511E−11 | 0.612 |
| NFL | 2 | 1.608 | 0.184 | 1.116 | 0.195 | 1.434 | 0.196 | 0.067 | 0.517 | 0.251 |
| CHI3L1 | 0 | 1.559 | 0.146 | 0.577 | 0.155 | 0.494 | 0.154 | 6.979E−06 | 1.098E−06 | 0.704 |

n.a. is not applicable.
Proportions were tested with chi2 tests, continuous variables with linear models.

The invention claimed is:

1. A method of treating a patient comprising administering a β-secretase inhibitor, an immune-modulating agent, an anti-tau and/or anti-beta amyloid antibody, a block copolymer and/or a corticosteroid to the patient suffering from a progressive neurodegenerative disease, comprising the steps of:

(a)—subtyping a sample of a patient suffering from a progressive neurodegenerative disease, comprising the steps of:

(a1)—providing a sample from the patient, whereby the sample comprises gene expression products of said patient;

(a2)—determining a level of expression for at least three gene expression products listed in Table 2, wherein said at least three gene expression products listed in Table 2 comprise CHGA, MASP1, and PLG;

(a3)—comparing said determined levels of expression of each of the at least three gene expression products to a reference level of expression of each of the three gene expression products in a reference sample; and (a4)—identifying a disease subtype, wherein the disease subtype is in a hyperplastic subgroup, a neuroinflammation subgroup or a BBB dysfunction subgroup, by comparison of the determined levels of expression level and the level of expression in a reference sample, thereby requiring treatment according to step (b); and (b) administering a β-secretase inhibitor when the patient is subtyped in a hyperplastic subgroup, administering an immune-modulating agent when the patient is subtyped in a neuroinflammation subgroup, and administering an anti-tau and/or anti-beta amyloid antibody or a block copolymer and/or a corticosteroid when the patient is subtyped in the BBB dysfunction subgroup, wherein the immune-modulating agent is PD-1, PD-L1 and/or CTLA-4 targeting antibodies, and/or p38 MAPK inhibitors, wherein the block copolymer is poly(ethylene oxide) and/or poly(propylene oxide), and wherein the corticosteroid is dexamethasone, methylprednisolone, prednisone, prednisolone, cortisol, cortisone, betamethasone, triamcinolone, fludrocortisone acetate and/or deoxycorticosterone acetate.

2. The method according to claim 1, wherein the sample from the patient is or comprises a bodily fluid.

3. The method according to claim 1, wherein the gene expression products are proteins.

4. The method according to claim 1, wherein the gene expression products are CHGA, MASP1, and PLG.

5. The method according to claim 1, wherein a level of expression for the at least three gene expression products is determined with the aid of an antibody or a functional part or equivalent thereof.

6. The method according to claim 5, wherein the antibody or a functional part or equivalent thereof is present on beads or on monolithic material.

7. The method according to claim 1, wherein a level of expression for the at least three gene expression products is determined by flow cytometric immunoassay (FCIA).

8. The method according to claim 1, wherein determination of a level of expression for the at least three gene expression products further comprises mass spectrometry.

9. The method according to claim 1, wherein the progressive neurodegenerative disease is Alzheimer's disease.

10. The method according to claim 2, wherein the bodily fluid is cerebrospinal fluid (CSF).

* * * * *